(12) United States Patent
Peng et al.

(10) Patent No.: US 8,900,481 B2
(45) Date of Patent: Dec. 2, 2014

(54) MONODISPERSE CORE/SHELL AND OTHER COMPLEX STRUCTURED NANOCRYSTALS AND METHODS OF PREPARING THE SAME

(75) Inventors: Xiaogang Peng, Fayetteville, AR (US); Jianqing Li, Los Angeles, CA (US); David Battaglia, Fayetteville, AR (US); Y. Andrew Wang, Fayetteville, AR (US); Yunjun Wang, Fayetteville, AR (US)

(73) Assignee: Board of Trustees of The University of Arkansas, Little Rock, AR (US)

( * ) Notice: Subject to any disclaimer, the term of this patent is extended or adjusted under 35 U.S.C. 154(b) by 300 days.

(21) Appl. No.: 12/722,005

(22) Filed: Mar. 11, 2010

(65) Prior Publication Data

US 2010/0171077 A1 Jul. 8, 2010

Related U.S. Application Data

(62) Division of application No. 10/763,068, filed on Jan. 22, 2004, now Pat. No. 7,767,260.

(60) Provisional application No. 60/442,146, filed on Jan. 22, 2003.

(51) Int. Cl.
C09K 11/02 (2006.01)
C09K 11/08 (2006.01)
(Continued)

(52) U.S. Cl.
CPC .......... C09K 11/883 (2013.01); C30B 29/605 (2013.01); C09K 11/565 (2013.01); H01S 5/30 (2013.01); G01N 33/588 (2013.01); C09K 11/703 (2013.01); H01S 3/169 (2013.01); H01L 33/28 (2013.01); C09K 11/7414 (2013.01); C30B 7/00 (2013.01); B82Y 30/00 (2013.01); *H01L 31/0352* (2013.01); *H01L 33/18* (2013.01); *H01L 31/036* (2013.01); *C09K 11/02* (2013.01); *B82Y 15/00* (2013.01)
USPC ....... 252/301.4 R; 252/301.6 R; 252/301.4 S; 252/301.6 S

(58) Field of Classification Search
USPC ........ 252/301.4 R, 301.4 S, 301.4 F, 301.6 R, 252/301.6 S, 301.6 F
See application file for complete search history.

(56) References Cited

U.S. PATENT DOCUMENTS 6,251,303 B1 * 6/2001 Bawendi et al. ........ 252/301.4 R
6,306,610 B1 * 10/2001 Bawendi et al. ............... 435/7.1
(Continued)

OTHER PUBLICATIONS

Little. Formation of quantum-dot quantum-well heteronanostructures with large lattice mismatch: ZnS/CdS/ZnS. Journal of Chemical Physics vol. 114, No. 4 Jan. 22, 2001.*

(Continued)

*Primary Examiner* — Matthew E Hoban
(74) *Attorney, Agent, or Firm* — Smith Moore Leatherwood LLP; Clint Wimbish

(57) ABSTRACT

The present invention provides new compositions containing nearly monodisperse colloidal core/shell semiconductor nanocrystals with high photoluminescence quantum yields (PL QY), as well as other complex structured semiconductor nanocrystals. This invention also provides new synthetic methods for preparing these nanocrystals, and new devices comprising these compositions. In addition to core/shell semiconductor nanocrystals, this patent application also provides complex semiconductor nanostructures, quantum shells, quantum wells, doped nanocrystals, and other multiple-shelled semiconductor nanocrystals.

37 Claims, 18 Drawing Sheets

(51) Int. Cl.

| | |
|---|---|
| *C09K 11/54* | (2006.01) |
| *C09K 11/56* | (2006.01) |
| *C09K 11/70* | (2006.01) |
| *C09K 11/72* | (2006.01) |
| *C09K 11/77* | (2006.01) |
| *C30B 29/60* | (2006.01) |
| *H01S 5/30* | (2006.01) |
| *G01N 33/58* | (2006.01) |
| *C09K 11/88* | (2006.01) |
| *C09K 11/74* | (2006.01) |
| *C30B 7/00* | (2006.01) |
| *B82Y 30/00* | (2011.01) |
| *H01L 31/0352* | (2006.01) |
| *H01L 31/036* | (2006.01) |
| *B82Y 15/00* | (2011.01) |
| *H01S 3/16* | (2006.01) |
| *H01L 33/28* | (2010.01) |
| *H01L 33/18* | (2010.01) |

(56) References Cited

U.S. PATENT DOCUMENTS 7,160,613 B2 *   1/2007   Bawendi et al. ............... 428/403
7,470,379 B2 * 12/2008   Anderson et al. ....... 252/301.6 S
7,601,424 B2 * 10/2009   Bawendi et al. ............... 428/403

OTHER PUBLICATIONS

Dabbousi. (CdSe)ZnS Core-Shell Quantum Dots: Synthesis and Characterization of a Size Series of Highly Luminescent Nanocrystallites. J. Phys. Chem. B 1997, 101, 9463-9475.*

Fedotov. Fractionation and characterization of nano- and microparticles in liquid media. Anal. Bioanal Chem. 400, 1787-1804.*

Schooss. Quantum-dot quantum well CdS/HgS/CdS: Theory and experiment. Phys. Rev. B 49, 17072-17078 (1994).*

Synthesis and Characterization of Monodisperse Nanocrystals and Close-Packed Nanocrystal Assemblies. Annual Rev. Mater. Si 2000. 30 545-610.*

Mews. Preparation, Characterization, and Photophysics of the Quantum Dot Quantum Well System CdS/HgS/CdS. J Phs Chem 1994, 98, 934-941.*

Epitaxial Growth of Highly Luminescent CdSe/CdS Core/Shell Nanocrystals with Photostability and Electronic Accessibility. J. Am. Chem. Soc. 1997, 119, 7019-7029.*

Sashchiuk. Synthesis and characterization of PbSe and PbSe/PbS core—shell colloidal nanocrystals. Journal of Crystal Growth 240 (2002) 431-438.*

Malik. A Simple Route to the Synthesis of Core/Shell Nanoparticles of Chalcogenides.Chem. Mater. 2002, 14, 2004-2010.*

* cited by examiner

MONODISPERSE CORE/SHELL AND OTHER COMPLEX STRUCTURED NANOCRYSTALS AND METHODS OF PREPARING THE SAME

PRIOR RELATED U.S. APPLICATION DATA

This application is a divisional application of U.S. patent application Ser. No. 10/763,068, filed Jan. 22, 2004, which claims priority to U.S. Patent Application Ser. No. 60/442,146, filed Jan. 22, 2003, which is incorporated by reference herein in its entirety.

STATEMENT OF GOVERNMENT LICENSE RIGHTS

The inventors received partial funding support through the National Science Foundation (Grant No. CHE0101178) and support through the joint Oklahoma University-University of Arkansas Center for Semiconductor Physics in Nanostructures. The Federal Government may retain certain license rights in this invention.

TECHNICAL FIELD OF THE INVENTION

The present invention relates to semiconductor nanocrystalline materials and to methods of making and using such materials.

BACKGROUND OF THE INVENTION

Colloidal semiconductor nanocrystals are nanometer-sized fragments of the corresponding bulk crystals, which have generated fundamental interest for their promise in developing advanced optical materials. The size-dependent emission is probably the most attractive property of semiconductor nanocrystals, for example, differently sized CdSe nanocrystals can be prepared that emit from blue to red, with comparatively pure color emissions. These nanocrystal-based emitters can be used for many purposes, such as for light-emitting diodes, lasers, biomedical tags, and the like.

One type of useful nanocrystalline material is the core/shell nanocrystal, which features a nanocrystalline core of one type material, coated with a shell of another type material. Core/shell nanocrystals are representative of a number of different complex structured nanocrystals, such as core/shell/shell structured materials, the architectures of which are aimed at providing fine control over the nanocrystal's photophysical properties. However, synthetic methods for preparing high quality, nearly monodisperse core/shell and other complex structured nanocrystals have lagged behind those available for the synthesis of plain core nanocrystals.

What are needed are improved methods to produce high quality, highly monodisperse core/shell and other complex structured nanocrystals that provide materials that approach the same high quality as the plain core nanocrystals currently available. In particular, synthetic techniques are needed that allow the preparation of these complex structured nanocrystals to approach the same level of control over fundamental parameters such as, crystallinity, size and size distribution, as that attained in the synthesis of plain core nanocrystals. The availability of such synthetic methods should improve the quality of known core/shell structures, and should generate many unexplored nanostructures.

SUMMARY OF THE INVENTION

Core/shell semiconductor nanocrystals, in which the core composition differs from the composition of the shell that surrounds the core, are useful for many optical applications. If the band offsets of the core/shell structures are type-I, and the shell semiconductor possesses a higher bandgap than the core material does, then the photo-generated electron and hole inside a nanocrystal will be mostly confined within the core. As used herein, type-I band offsets refer to a core/shell electronic structure wherein both conduction and valence bands of the shell semiconductor are simultaneously either higher or lower than those of the core semiconductor. Consequently, conventional core/shell nanocrystals can show high photoluminescence (PL) and electroluminescence efficiencies and can be more stable against photo-oxidation than "plain core" semiconductor nanocrystals comprising a single material, provided that the bandgap of the core semiconductor is smaller than that of the shell semiconductor. See, for example: Hines, M. A.; Guyot-Sionnest, P. *J. Phys. Chem.* 1996, 100, 468; Peng, X.; Schlamp, M. C.; Kadavanich, A. V.; Alivisatos, A. P. *J. Am. Chem. Soc.* 1997, 119, 7019-7029; Dabbousi, B. O.; RodriguezViejo, J.; Mikulec, F. V.; Heine, J. R.; Mattoussi, H.; Ober, R.; Jensen, K. F.; Bawendi, M. G. *J. Phys. Chem. B* 1997, 101, 9463-9475; Micic, O. I.; Smith, B. B.; Nozik, A. J. *J. Phys. Chem. B* 2000, 104, 12149-12156; Cao, Y.; Banin, U. *J. Am. Chem. Soc.* 2000, 122, 9692-9702; Manna, L.; Scher, E. C.; Li, L.-S.; Alivisatos, A. P. *J. Am. Chem. Soc.* 2002, 124, 7136-7145; Cumberland, S. L.; Hanif, K. M.; Javier, A.; Khitrov, G. A.; Strouse, G. F.; Woessner, S. M.; Yun, C. S. *Chem. Mater.* 2002, 14, 1576-1584; Reiss, P.; Bleuse, J.; Pron, A. *Nano Lett.* 2002, 2, 781-784; Schlamp, M. C.; Peng, X. G.; Alivisatos, A. P. *J. Appl. Phys.* 1997, 82, 5837-5842; Mattoussi, H.; Radzilowski, L. H.; Dabbousi, B. O.; Thomas, E. L.; Bawendi, M. G.; Rubner, M. F. *J. Appl. Phys.* 1998, 83, 7965-7974; Tesster, N.; Medvedev, V.; Kazes, M.; Kan, S.; Banin, U. *Science* 2002, 295, 1506-1508; each of which is incorporated by reference herein, in its entirety.

Recent advancements in synthesis of semiconductor nanocrystals have made it possible to obtain highly luminescent plain core nanocrystals. (See, for example: Hines, M. A.; Guyot-Sionnest, P. *J. Phys. Chem. B* 1998, 102, 3655-3657; Talapin, D.; Rogach, A. L.; Kornowski, A.; Haase, M.; Weller, H. *Nano Lett.* 2001, 1, 207; Qu, L.; Peng, X. *J. Am. Chem. Soc.* 2002, 124, 2049-2055; each of which is incorporated by reference herein, in its entirety.) However, plain core nanocrystals may suffer from lack of stability and processability. While not intending to be bound by theory, it is possible that the underlying causes of this instability and poor processability may be intrinsic. Further, plain core nanocrystals may also be chemically and thermally less stable than a corresponding core/shell nanocrystal comprising a core of the same composition as the plain core nanocrystal, largely as a result of their lack of a protective coating of another, more stable, material. Therefore, core/shell nanocrystals are likely to be the desired structures when the nanocrystals must either undergo complicated chemical treatments, such as in bio-medical applications, or when the nanocrystals are constantly excited, such as for LEDs and lasers. (See, for example: Bruchez, M.; Moronne, M.; Gin, P.; Weiss, S.; Alivisatos, A. P. *Science* 1998, 281, 2013-2016; Chan, W. C. W.; Nie, S. M. *Science* 1998, 281, 2016-2018; Mattoussi, H.; Mauro, J. M.; Goldman, E. R.; Anderson, G. P.; Sundar, V. C.; Mikulec, F. V.; Bawendi, M. G. *J. Am. Chem. Soc.* 2000, 122, 12142; Han, M.; Gao, X.; Su, J. Z.; Nie, S, *Nat. Biotechnol.* 2001, 19, 631-635; Schlamp, M. C.; Peng, X. G.; Alivisatos, A. P. *J. Appl. Phys.* 1997, 82, 5837-5842; Mattoussi, H.; Radzilowski, L. H.; Dabbousi, B. O.; Thomas, E. L.; Bawendi, M. G.; Rubner, M. F. *J. Appl. Phys.* 1998, 83, 7965-7974; Tesster, N.; Medvedev, V.; Kazes, M.; Kan, S.; Banin, U. *Science* 2002, 295, 1506-1508; Klimov, V. I.; Mikhailovsky, A. A.;

Xu, S.; Malko, A.; Hollingsworth, J. A.; Leatherdale, C. A.; Eisler, H. J.; Bawendi, M. G. *Science* 2000, 290, 314-317; each of which is incorporated by reference herein, in its entirety.)

The present invention addresses many of the current limitations in obtaining highly monodisperse core/shell nanocrystals, quantum shells, quantum wells, doped nanocrystals, and other complex structured nanocrystals by providing new synthetic strategies, nanocrystalline structures, compositions, devices, and methods encompassing these materials.

In one aspect, for example, this invention provides new compositions containing highly monodisperse colloidal core/shell semiconductor nanocrystals with high photoluminescence quantum yields (PL QY), as well as other complex structured semiconductor nanocrystals. In another aspect, for example, this invention provides a high level of control over the thickness of a shell which overcoats a nanocrystalline core, and a high level of control over the thickness of additional shells which overcoat any underlying shells. In comparison, the size, size distribution, and optical properties of core/shell nanocrystals gown using existing methods become significantly worse than the core or the core/shell nanocrystals coated with a thin layer of shell, typically, for example, one to two monolayers. (See, for example: Hines, M. A.; Guyot-Sionnest, P. *J. Phys. Chem.* 1996, 100, 468; Peng, X.; Schlamp, M. C.; Kadavanich, A. V.; Alivisatos, A. P. *J. Am. Chem. Soc.* 1997, 119, 7019-7029; Dabbousi, B. O.; RodriguezViejo, J.; Mikulec, F. V.; Heine, J. R.; Mattoussi, H.; Ober, R.; Jensen, K. F.; Bawendi, M. G. *J. Phys. Chem. B* 1997, 101, 9463-9475; Micic, O. I.; Smith, B. B.; Nozik, A. J. *J. Phys. Chem. B* 2000, 104, 12149-12156; Cao, Y.; Banin, U. *J. Am. Chem. Soc.* 2000, 122, 9692-9702; Manna, L.; Scher, E. C.; Li, L.-S.; Alivisatos, A. P. *J. Am. Chem. Soc.* 2002, 124, 7136-7145; Cumberland, S. L.; Hanif, K. M.; Javier, A.; Khitrov, G. A.; Strouse, G. F.; Woessner, S. M.; Yun, C. S. *Chem. Mater.* 2002, 14, 1576-1584; Reiss, P.; Bleuse, J.; Pron, A. *Nano Lett.* 2002, 2, 781-784.)

In another aspect, for example, this invention also provides new synthetic methods for preparing highly monodisperse colloidal core/shell semiconductor nanocrystals, and new devices comprising these compositions. In this aspect, for example, this invention also provides a high level of control over the thickness of a shell which overcoats a nanocrystalline core, and a high level of control over the thickness of additional shells which overcoat any underlying shells. In addition to core/shell semiconductor nanocrystals, this patent application also provides complex semiconductor nanostructures, quantum shells, quantum wells, doped nanocrystals, and other multiple-shelled semiconductor nanocrystals. This invention, therefore, provides new materials, new methods, and new devices comprising the new materials of this invention.

In one aspect, the present invention encompasses a method for preparing core/shell and other complex structured nanocrystals, referred to herein as either successive ionic layer adsorption and reaction (SILAR), or solution atomic layer epitaxy (SALE), for the growth of high quality core/shell nanocrystals of compound semiconductors. This solution phase epitaxial method differs, in one aspect, from more traditional approaches in that growth of the shell material onto the core nanocrystal was achieved in one monolayer a time, by alternating injections of the cationic and anionic solutions into the reaction mixture.

The SILAR method can be applied to a wide range of core/shell crystalline materials, and can be used to prepare core/multiple shell materials, such as core/shell/shell, core/shell/shell/shell, core/shell/shell/shell/shell compositions, and the like. The principles of SILAR (or SALE) were demonstrated by the preparation of, among other things, highly monodisperse CdSe/CdS core/shell nanocrystals, in which the shell-thickness-dependent optical properties were used as probes of the nanocrystal size and size distribution.

As used herein, the terminology "composition 1/composition 2" is employed to reflect the composition of the core material (composition 1) and the shell material (composition 2). When more than one shell is present over a nanocrystalline core, the terminology "composition 1/composition 2/composition 3" is used herein to reflect the composition of the core material (composition 1), the first shell material (composition 2), and the third shell material (composition 3). Compositions with more than two shell layers are described using a similar notation method.

In one aspect, the present invention provides nanocrystals comprising a variety of compositions and characterized by a variety of structural motifs that exhibit a narrow size distribution, that is, are highly monodisperse. For example, the narrow size distribution of core/shell nanocrystals, such as CdSe/CdS, CdS/CdSe, or CdS/CdSe/CdS, prepared according to this invention was maintained even after at least about 15 monolayers of the shell were grown, equivalent to about a forty-fold volume increase for a 3.5 nm core nanocrystal. The epitaxial growth of the core/shell structures was verified by optical spectroscopy, transmission electron microscopy (TEM), and x-ray diffraction (XRD) techniques. The photoluminescence quantum yield (PL QY) of the as-prepared CdSe/CdS core/shell nanocrystals ranged from about 20% to about 50%. As used herein, the terminology "as-prepared" nanocrystals or nanocrystalline products refer to those nanocrystal samples dissolved in the original reaction mixture or diluted by a solvent without the removal of any unreacted reactants and the side products. Further, several types of brightening phenomena were observed for the as-prepared CdSe/CdS core/shell nanocrystals which further boosted their photoluminescence quantum yield (PL QY). In addition, the processability of the CdSe/CdS core/shell nanocrystals was found to be superior in comparison to the highly luminescent CdSe plain core nanocrystals.

This invention further encompasses the application of SILAR technology to many other types of core/shell structures, including but not limited to CdSe/ZnSe, CdSe/ZnS, InP/CdS, InAs/CdS, InAs/InP, InAs/CdSe, CdS/CdSe, CdS/InP, CdS/CdSe/CdS, CdSe/ZnS/CdSe, CdSe/ZnS/CdSe/ZnS, ZnSe/Zn$_x$Cu$_{1-x}$Se/ZnSe, and the like. The core/shell structures of the types CdS/CdSe, CdS/InP, and the like, are examples of a type of quantum structures termed "quantum shells." Nanocrystalline CdS/CdSe/CdS core/shell/shell structures are examples of colloidal quantum wells. Nanocrystalline ZnSe/Zn$_x$Cu$_{1-x}$Se/ZnSe core/shell/shell structures are examples of doped nanocrystals. Nanocrystalline CdSe/ZnS/CdSe and CdSe/ZnS/CdSe/ZnS structures represent examples of dual emitting nanocrystals. According to the present invention, synthetic methods are provided for precise control of the radial distribution of the dopants.

Likely due to the large band offsets between the core and shell semiconductors, the photoluminescence quantum yields (PL QY) of the CdSe/ZnS and CdSe/ZnSe core/shell nanocrystals were found to be even higher than that of the CdSe/CdS system. For the core/shell nanocrystals with III-V semiconductor nanocrystals as the cores, the PL QY and photochemical stability of the core/shell nanocrystals were found to be significantly improved as compared to the plain core III-V semiconductor nanocrystals.

In one example, the photoluminescence quantum yield (PL QY) of the CdS/CdSe quantum shells according to this invention was found to be as high as 20%. The epitaxial growth of an extra shell of CdS onto the CdS/CdSe quantum shells, which formed colloidal quantum wells, further enhanced the PL of the CdSe layer to as high as about 50%.

Further, air-stable, relatively inexpensive, and safe precursors and solvents were found to be compatible with SILAR technology, and the syntheses could readily be performed on multigram scales. These factors made the SILAR technology of this invention very cost effective in comparison to existing synthetic schemes.

In one aspect, the present invention provides a composition comprising core/shell nanocrystals, wherein:

the nanocrystals comprise a core material and a shell material overcoating the core material, each of which is independently selected from a II/VI compound or a III/V compound, the band gap of the core material is less than the band gap of the shell material; and the thickness of the shell material is from 1 to about 15 monolayers.

In another aspect, the present invention provides the core/shell nanocrystals themselves.

In another aspect, for example, this invention provides a composition comprising nanocrystalline, core/shell quantum shells, wherein:

the quantum shells comprise a core material and a shell material overcoating the core material;

the core material comprises a stable, nanometer-sized inorganic solid;

the shell material overcoating the core material is selected from a II/VI compound or a III/V compound;

the band gap of the core material is greater than the band gap of the shell material;

the thickness of the shell material is from 1 to about 15 monolayers; and the as-prepared quantum shells having the shell thickness greater than 1 monolayer exhibit a photoluminescence that is substantially limited to a bandgap emission, with a photoluminescence quantum yield (PL QY) up to about 20%.

In another aspect, the present invention provides a composition comprising nanocrystalline, core/shell/shell quantum wells, wherein:

the quantum wells comprise a core material, a first shell material overcoating the core material, and a second shell material overcoating the first shell material;

the core material comprises a stable, nanometer-sized inorganic solid;

the first shell material and the second shell material are independently selected from a II/VI compound or a III/V compound;

the band gap of the first shell material is less than the band gap of the core material and less than the band gap of the second shell material; and the as-prepared quantum wells exhibit a photoluminescence that is substantially limited to a bandgap emission, with a photoluminescence quantum yield (PL QY) up to about 50%.

In still another aspect, this invention provides a composition comprising nanocrystalline, core/multiple shell quantum wells, wherein:

the quantum wells comprise a core material, a first shell material overcoating the core material, a second shell material overcoating the first shell material, and optionally comprising additional shell materials sequentially overcoating underlying shells;

the core material comprises a stable, nanometer-sized inorganic solid;

the first shell material and the second shell material are independently selected from a II/VI compound or a III/V compound;

any additional shells are independently selected from a II/VI compound or a III/V compound; and the band gap of any shell material is less than the band gap of the both adjacent core or shell materials, or greater than the band gap of the both adjacent core or shell materials.

In a further aspect, this invention provides a composition comprising radially-doped, or simply, "doped", core/shell/shell nanocrystals wherein:

the radially-doped nanocrystals comprise a core material, a first shell material overcoating the core material, and a second shell material overcoating the first shell material;

the core material comprises a compound of the formula $M^1_x E_y$, wherein $M^1$ is selected from a metal, E is selected from a non-metal, and x and y are dictated by the stoichiometry of the compound;

the first shell material comprises a compound of the formula $M^1_{x-z} M^2_z E_y$, wherein $M^2$ is selected from a transition metal or a mixture thereof, $0 \leq z < x$, and $M^2$ is different than $M^1$; and the second shell material comprises a compound of the formula $M^1_{x-q} M^3_q E_y$, wherein $M^3$ is selected from a transition metal, a rare earth metal, or a mixture thereof, $0 \leq q \leq x$, and x is not equal to q when $M^2$ is the same as $M^3$.

In yet another aspect, this invention provides a composition comprising radially-doped, core/multiple shell nanocrystals wherein:

the radially-doped nanocrystals comprise a core material, a first shell material overcoating the core material, a second shell material overcoating the first shell material, and a third shell material overcoating the second shell material;

the core material comprises a compound of the formula $M^1_a E^1_b$, wherein $M^1$ is selected from a group II or group III metal; $E^1$ is selected from a non-metal; and a and b are dictated by the stoichiometry of the compound;

the first shell material comprises a compound of the formula $M^1_{a-c} M^2_c E^1_b$, wherein $M^2$ is selected from at least one transition metal; $0 \leq c < a$; and $M^2$ is different than $M^1$;

the second shell material comprises a compound of the formula $M^3_{d-f} M^4_f E^1_e$, wherein $M^3$ is selected from a group II or group III metal; $M^4$ is selected from a transition metal, a rare earth metal, or a mixture thereof; d and e are dictated by the stoichiometry of the compound $M^3_d E^3_e$; and $0 \leq f < d$;

the third shell material comprises a compound of the formula $M^5_{g-i} M^6_i E^5_h$, wherein $M^5$ is selected from a group II or group III metal; $M^6$ is selected from a transition metal, a rare earth metal, or a mixture thereof; g and h are dictated by the stoichiometry of the compound $M^5_g E^5_h$; and $0 \leq i < g$;

wherein the bandgap of the third shell material is greater than the bandgap of the core material, greater than the bandgap of the first shell material, and greater than the bandgap of the second shell materials; and wherein the thicknesses of the first shell material, the second shell material, and the third shell material are independently varied between 0 and 15 monolayers. In another aspect related to these radially-doped core/multiple shell nanocrystals: a) i) $M^1$ can be selected from Zn, Cd, or Hg, and $E^1$ is selected from O, S. Se, or Te; or ii) $M^1$ can be selected from Ga and In, and $E^1$ is selected from N, P and As; and b) $M^2$ can be selected from Mn, Fe, Co, Ni, Pd, Pt, Cu, Al, Ag, or Au, or a rare earth metal.

In yet another aspect, related to these radially-doped core/multiple shell nanocrystals, $M^1_a E^1_b$ can be selected from CdSe, CdS, CdTe, ZnS, ZnSe, ZnTe, HgS, HgSe, HgTe, InAs, InP, GaAs, GaP, ZnO, CdO, HgO, $In_2O_3$, $TiO_2$, or a rare earth oxide.

In another aspect related to these radially-doped core/multiple shell nanocrystals, the radially-doped, core/multiple shell nanocrystals can comprise $ZnSe/Zn_{a-c}M^2_cSe/ZnSe$, $ZnSe/Zn_{a-c}M^2_cSe/ZnS$, $ZnO/Zn_{a-c}M^2_cO/ZnO$, $ZnO/Zn_{a-c}M^2_cO/ZnS$, $TiO_2/Ti_{a-c}M^2_cO_2/TiO_2$, and wherein $M^2$ is selected from Mn, Fe, Co, Ni, Pd, Pt, Al, Cu, Ag, or Au, or a rare earth metal.

In still another aspect, this invention provides a composition comprising core/multiple shell nanocrystals which are optionally doped at the core and optionally doped at any shell. In this aspect, the present invention provides a composition comprising radially-doped, core/multiple shell nanocrystals, comprising:

1) a core material having the formula $M^1_{a-c}M^2_cE^1_b$, wherein:
   a) $M^1$ is selected from a metal, $E^1$ is selected from a non-metal, and a and b are dictated by the stoichiometry of the compound $M^1_aE^1_b$;
   b) $M^2$ is selected from a transition metal, a rare earth metal, or a mixture thereof; and $M^2$ is different than $M^1$; and
   c) $0 \leq c < a$;

2) an optional first shell material overcoating the core material, having the formula $M^3_{d-f}M^4_fE^3_e$, wherein:
   a) $M^3$ is selected from a metal, $E^3$ is selected from a non-metal, and d and e are dictated by the stoichiometry of the compound $M^3_dE^3_e$;
   b) $M^4$ is selected from a transition metal, a rare earth metal, or a mixture thereof; and $M^4$ is different than $M^3$; and
   c) $0 \leq f < d$;

3) an optional second shell material overcoating the optional first shell material, having the formula $M^5_{g-i}M^6_iE^5_h$, wherein:
   a) $M^5$ is selected from a metal, $E^5$ is selected from a non-metal, and g and h are dictated by the stoichiometry of the compound $M^5_gE^5_h$;
   b) $M^6$ is selected from a transition metal, a rare earth metal, or a mixture thereof; and $M^6$ is different than $M^5$; and
   c) $0 \leq i < g$;

4) an optional third shell material overcoating the optional second shell material, having the formula $M^7_{j-l}M^8_lE^7_k$, wherein:
   a) $M^7$ is selected from a metal, $E^7$ is selected from a non-metal, and j and k are dictated by the stoichiometry of the compound $M^7_jE^7_k$;
   b) $M^8$ is selected from a transition metal, a rare earth metal, or a mixture thereof; and $M^8$ is different than $M^7$; and
   c) $0 \leq l < j$; and 5) an optional fourth shell material overcoating the optional third shell material, having the formula $M^9_{m-o}M^{10}_oE^9_n$, wherein:
   a) $M^9$ is selected from a metal, $E^9$ is selected from a non-metal, and m and n are dictated by the stoichiometry of the compound $M^9_mE^9_n$;
   b) $M^{10}$ is selected from a transition metal, a rare earth metal, or a mixture thereof; and $M^{10}$ is different than $M^9$; and
   c) $0 \leq o < m$.

In another aspect, this invention also provides a composition comprising core/shell/shell dual-emitting nanocrystals, wherein:

the nanocrystals comprise a core material, a first shell material overcoating the core material, and a second shell material overcoating the first shell material, each of which is independently selected from a II/VI compound or a III/V compound;

the band gap of the first shell material is greater than the band gap of the core material and greater than the band gap of the second shell material; and the as-prepared dual-emitting nanocrystals exhibit a photoluminescence comprising bandgap emission peaks.

In this aspect, the additional shells are independently selected from selected from a II/VI compound or a III/V compound; and the band gap of the additional shell material is greater than the band gap of the second shell material.

In yet another aspect, this invention provides a composition comprising core/shell/shell/shell dual-emitting nanocrystals, wherein:

the nanocrystals comprise a core material, a first shell material overcoating the core material, a second shell material overcoating the first shell material, and a third shell material overcoating the second shell material, each of which is independently selected from a II/VI compound or a III/V compound;

the band gap of the first shell material and the band gap of the third shell material are less than the band gap of the core material and are less than the band gap of the second shell material; and the as-prepared dual-emitting nanocrystals exhibit a photoluminescence comprising bandgap emissions.

In one aspect, the dual-emitting nanocrystals can comprise up to at least about 12 to 15 additional shells, wherein the additional shells are typically independently selected from a II/VI compound or a III/V compound; and wherein the band gap of the additional shell material is greater than the band gap of the second shell material.

In another aspect, this invention also encompasses a method for preparing core/shell nanocrystals having the formula $M^1X^1/M^2X^2$, comprising:

a) providing a solution of core nanocrystals of the formula $M^1X^1$;

b) forming a first monolayer of a shell material $M^2X^2$ by contacting the core nanocrystals, in an alternating manner, with a cation ($M^2$) precursor solution in an amount effective to form a monolayer of the cation, and an anion ($X^2$) precursor solution in an amount effective to form a monolayer of the anion; and c) optionally forming subsequent monolayers of shell material $M^2X^2$ by contacting the core/shell nanocrystals, in an alternating manner, with a cation ($M^2$) precursor solution in an amount effective to form a monolayer of the cation, and an anion ($X^2$) precursor solution in an amount effective to form a monolayer of the anion;

wherein $M^1X^1$ comprises a stable, nanometer-sized inorganic solid;

wherein $M^2X^2$ is selected from a II/VI compound or a III/V compound; and wherein $M^1X^1$ and $M^2X^2$ are different. In this aspect, the cation precursor solution can optionally contain at least one ligand, and the anion precursor solution can optionally contain at least one ligand.

In still another aspect, this invention encompasses a method for preparing core/shell/shell nanocrystals having the formula $M^1X^1/M^2X^2/M^3X^3$ comprising:

a) providing a solution of core nanocrystals of the formula $M^1X^1$;

b) forming at least one monolayer of a first shell material $M^2X^2$ by contacting the core nanocrystals, in an alternating manner, with a first cation ($M^2$) precursor solution in an amount effective to form a monolayer of the first cation, and a first anion ($X^2$) precursor solution in an amount effective to form a monolayer of the first anion; and c) forming at least one monolayer of a second shell material $M^3X^3$ by contacting the core nanocrystals, in an alternating manner, with a second cation ($M^3$) precursor solution in an amount effective to form a monolayer of the second cation, and an second anion ($X^3$) precursor solution in an amount effective to form a monolayer of the first anion;

wherein $M^1X^1$ comprises a stable, nanometer-sized inorganic solid;

wherein $M^2X^2$ and $M^3X^3$ are independently selected from a II/VI compound or a III/V compound; and wherein $M^1X^1$, $M^2X^2$, and $M^3X^3$ are different.

In yet another aspect, the present invention provides a method for preparing radially-doped core/shell/shell nanocrystals having the formula $M^1_x E_y / M^1_{x-z} M^2_z E_y / M^1_{x-q} M^3_q E_y$, comprising:

a) providing a solution of core nanocrystals of the formula $M^1_x E_y$, wherein $M^1$ is selected from a metal, E is selected from a non-metal, and x and y are dictated by the stoichiometry of the compound;

b) forming at least one monolayer of a doped first shell material of the formula $M^1_{x-z} M^2_z E_y$ by contacting the core nanocrystals, in an alternating manner, with a cation precursor solution in an amount effective to form a monolayer of the first cation doped with the second cation, and a first anion ($X^2$) precursor solution in an amount effective to form a monolayer of the first anion;

wherein the cation precursor solution comprises a first cation ($M^1$) precursor, a second cation ($M^2$) precursor, or a combination thereof, and wherein $M^2$ is selected from a transition metal or a mixture thereof, $0 \leq z < x$, and $M^2$ is different than $M^1$;

c) forming at least one monolayer of a second shell material of the formula $M^1_{x-q} M^3_q E_y$ by contacting the core/shell nanocrystals, in an alternating manner, with a first cation precursor solution in an amount effective to form a monolayer of the first cation, and an second anion ($X^3$) precursor solution in an amount effective to form a monolayer of the first anion;

wherein the first cation precursor solution optionally comprises a third cation ($M^3$) precursor selected from a transition metal, a rare earth metal, or a mixture thereof; and wherein $0 \leq q \leq x$, and x is not equal to q when $M^2$ is the same as $M^3$; and d) optionally repeating steps b and c to form additional shells overcoating the second shell.

Accordingly, it is one aspect of the present invention to provide new synthetic methods for preparing semiconductor core/shell and other complex structured nanocrystals that are characterized by high photoluminescence quantum yields.

It is another aspect of this invention is the development of new synthetic methods for preparing semiconductor core/shell and other complex structured nanocrystals that are nearly monodisperse.

It is a further aspect of this invention to provide a method for control over the stability of the photoluminescence emission of as-prepared semiconductor core/shell and other complex structured nanocrystals.

In one aspect, for example, this invention provides techniques for the growth of high quality core/shell nanocrystals, which may also be amenable for the growth of nanocrystals with very complex composition profile along the radial direction of the nanocrystals. For example, a colloidal quantum well can comprise a low bandgap semiconductor sandwiched between two high bandgap semiconductors, epitaxially grown on the surface of bulk single crystal substrate by molecular beam epitaxy or related techniques. Such structures are of great interest for their photophysical properties.

In another aspect, for example, the present invention provides methods for synthesizing complex structured doped nanocrystals, wherein the doping is effected in a given radial position. These "radially-doped" nanocrystalline materials are of interest for, among other things, for spintronics, atomic emitting materials, and the like. Thus, the present invention provides, in this aspect, a method for doping a nanocrystal in a given radial position in a controlled fashion.

In yet another aspect, the present invention provides synthetic methods for preparing high quality, highly monodisperse core/shell and other complex structured nanocrystals. In this aspect, for example, the methods of this invention allow a narrow size distribution of core/shell nanocrystals to be attained as the growth of a shell material proceeds.

The synthetic methods of the present invention provide for preparing high quality, nearly monodisperse core/shell and other complex structured nanocrystals. In this aspect, for example, the methods of this invention allow a narrow size distribution of core/shell nanocrystals to be attained as the growth of a shell material proceeds. While not intending to be bound by theory, it is believed that such a feature has been possible by, among other things, the substantial reduction or elimination of any homogeneous nucleation of the shell material that would otherwise provide a mixture of nanocrystals of core material and nanocrystals of shell material. In this aspect, essentially all the shell precursor material added into a solution of the core nanocrystals grows exclusively onto the core nanocrystals. Again, while not intending to be bound by theory, it is believed that nearly monodisperse core/shell and other complex structured nanocrystals have also been possible by, among other things, shell growth that not only proceeds at substantially the same rate, but also initiates at substantially the same time at each nanocrystalline core site.

Another aspect of this invention is the development of methods to correlate reaction conditions with the resulting PL QY of semiconductor core/shell nanocrystals, and to thereby impart control over nanocrystal quantum yield.

It is a further aspect of this invention to provide a method for control over the stability of the photoluminescence emission of as-prepared semiconductor core/shell nanocrystals.

Accordingly, it is one aspect of the present invention to provide new synthetic methods for preparing II-VI, III-V, and other types of semiconductor core/shell nanocrystals that are both nanometer size and highly monodisperse.

It is a further aspect of this invention to provide a method for synthesizing highly monodisperse, semiconductor core/shell nanocrystals utilizing inexpensive, low or limited toxicity precursors materials.

Yet another aspect of the present invention is the development of a method of synthesizing monodisperse semiconductor core/shell nanocrystals using non-coordinating solvents.

A further aspect of this invention is the development of a procedure for controlling the average size of the semiconductor core/shell nanocrystals prepared using non-coordinating solvents.

Another aspect of the present invention is the development of methods for synthesizing monodisperse core/shell nanocrystals comprising CdSe/CdS, CdSe/ZnSe, CdSe/ZnS, InP/CdS, InAs/CdS, InAs/InP, InAs/CdSe, CdS/CdSe, CdS/InP, and the like, with high quality and improved photoluminescence properties.

Still a further aspect of this invention is the synthesis of a new class of colloidal quantum structures referred to herein as "quantum shells," characterized by a large energy band gap offset between the core and shell materials, that is quantum shells are characterized by a large band gap for the core and a small band gap for the shell where the difference between these band gaps is substantial.

A further aspect of the present invention is the development of successive ionic layer adsorption and reaction (SILAR) methods, or solution atomic layer epitaxy (SALE) methods, for the growth of high quality core/shell nanocrystals of compound semiconductors, including quantum shells.

Still another aspect of this invention is the development of synthetic procedures for preparing core/shell and other complex structured nanocrystals that allow more environmentally innocuous precursors, ligands, and solvents to be employed, and that are convenient, less expensive, safer, faster, and more environmentally "green" than methods currently used.

This invention further provides, in one aspect, articles of manufacture comprising the nanocrystalline materials disclosed herein.

These and other features, aspects, objects and advantages of the present invention will become apparent after a review of the following detailed description of the disclosed embodiments and appended claims, in conjunction with the drawings described as follows.

DETAILED DESCRIPTION OF THE INVENTION

Figure 1:
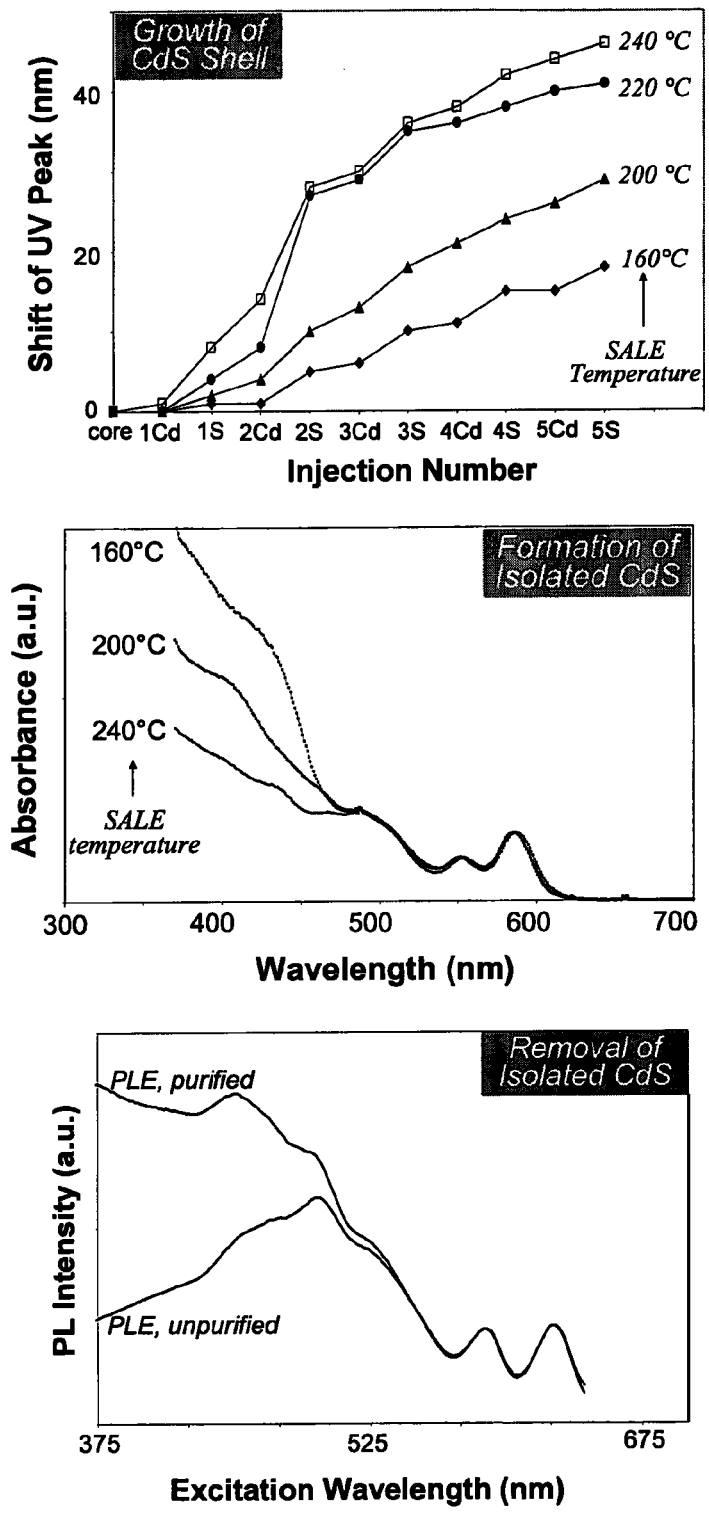
FIG. 1 illustrates the following. Top: The accumulative value of the red shift of the first absorption peak for CdSe/CdS nanocrystals due to the growth of CdS shell after each injection at different reaction temperatures. Middle: Formation of isolated CdS nanocrystals at relatively low temperatures, evidenced by the extremely high absorbance at high energy part even with thin CdS shell. Bottom: PLE (photoluminescence excitation) spectra of CdSe/CdS nanocrystals before and after the removal of isolated CdS particles.

The present invention addresses many of the current limitations in core/shell and related complex structured nanocrystals by providing new compositions, new methods, and new devices based on a synthetic strategy, termed "successive ionic layer adsorption and reaction" (SILAR) or "solution atomic layer epitaxy" (SALE), for the growth of high quality, highly monodisperse core/shell and other complex structured nanocrystals of compound semiconductors. This solution phase epitaxial method achieves growth of the shell material onto the core material typically one monolayer per reaction cycle, by alternating injections of the cationic and anionic solutions into the reaction mixture. One reaction cycle refers to two consecutive injections of the reaction precursors, one for the cationic (anionic) precursor solution and the following one for the anionic (cationic) precursor solution.

The Successive Ionic Layer Adsorption and Reaction (SI-LAR) Method and the Preparation and Properties of Core/Shell Nanocrystals Prepared Using SILAR In one embodiment, the present invention comprises core/shell nanocrystals and methods of preparing core/shell nanocrystals. In several examples, the CdSe/CdS core/shell nanocrystals are used as exemplary core/shell nanocrystals of this method.

It was discovered that although 1-octadecene (ODE) is a non-coordinating solvent, it provided good solubility for the core nanocrystals of CdSe, and for the two injection solutions comprising the cation precursor, cadmium oxide, and the anion precursor, elemental sulfur. Further, ODE has a large liquid range, relatively low cost, low toxicity, and low reactivity to precursors, thereby providing a more environmentally "green" synthesis than previous core/shell nanocrystal syntheses.

Relatively safe and inexpensive precursors for the growth of the CdS shell onto the CdSe core nanocrystals could also be used. In one aspect, this invention provides a method of preparing CdSe/CdS nanocrystals wherein the cation precursor was selected as CdO and the anion precursor was selected as elemental sulfur. In one aspect, for example, the injection solution of Cd was prepared by dissolving CdO in ODE using fatty acids, including but not limited to, stearic acid, oleic acid, and dodecanoic acid, as the ligands. Elemental sulfur could be dissolved in warm ODE directly, and the resulting solution was used as the sulfur injection solution. In this aspect, octadecylamine (ODA) was used as a ligand for the core/shell nanocrystals.

In one aspect, Example 1 illustrates a preparative method of this invention for the synthesis of the core CdSe nanocrystals, in which the CdSe nanocrystals were stabilized in solution by coating then with ODA ligands. In comparison to the TOPO (trioctylphosphine)-coated nanocrystals, these amine-coated cores yielded core/shell nanocrystals with significantly higher PL QY. (See, "Control of Photoluminescence Properties of CdSe Nanocrystals in Growth", Qu L., Peng, X., *J. Am. Chem. Soc.*, 2002, vol 124, p 2049, which is incorporated herein by reference in its entirety.)

Example 2 provides synthesis of the cadmium oxide (cation precursor) and sulfur (anion precursor) injection solutions, Example 3 describes the calculations performed in determining the injection procedure, including the amount of solution to be injected, using the two injection solutions.

Two loading methods were tested for adding the CdSe core nanocrystals into the reaction flask. The first loading method comprised loading the nanocrystals as a solution in hexanes, in which the nanocrystals had never been precipitated out of solution after their preparation. In this aspect, the purification of the core nanocrystals was performed by an extraction method described in Example 1. The second loading method comprised loading the nanocrystals in which the core nanocrystals had been purified by precipitation, followed by decantation of the supernatant, after which the purified precipitate was loaded into the reaction mixture. In this aspect, the first, solution-based loading approach generally provided better growth of high quality core/shell nanocrystals than the second method. For example, transmission electron microscopy (TEM) measurements revealed that aggregates and fused particles were formed by precipitation of the amine-coated CdSe nanocrystals by the second method. Although this invention encompasses nanocrystals prepared by either approach, the results disclosed herein for the core/shells using CdSe nanocrystal cores were obtained using the solution-based loading method.

Example 4 describes one aspect of the preparative method of this invention for the synthesis of CdSe/CdS core/shell nanocrystals using successive ionic layer adsorption and reaction (SILAR). Example 5 provides an example of how the SALE method may be used to prepare multigram quantities of the CdSe/CdS core/shell nanocrystals.

In one aspect of this invention, there were typically two methods by which SILAR methodology was used to prepare colloidal core/shell nanocrystals of the present invention. As disclosed herein, the core was coated or contacted with a first shell monolayer by alternately contacting the core nanocrystal with a cation precursor solution and an anion precursor solution, in which both cation and anion precursor solution were employed in an amount sufficient to form one monolayer of the shell material. This method was useful when monolayer accuracy was desired. However, in another aspect, it is also possible to grow a shell layer with less than one monolayer thickness by adding less precursors in one injection cycle. In addition, when monolayer accuracy was not required, multiple shell monolayers were coated onto a core by alternately contacting the core nanocrystal with a cation precursor solution in an amount sufficient to form the desired shell thickness, and contacting the core nanocrystal with an anion precursor solution in an amount sufficient to form the desired shell thickness. In this case, multiple monolayers of shell could be conveniently added.

The reaction temperature for the growth of the CdS shell onto CdSe nanocrystals through SILAR in ODE was investigated. FIG. 1 (top plot) illustrates the evolution of the UV-Vis peak position of the core/shell nanocrystals, representing the change in shell thickness since an identical core sample was used in each plot, after each injection of either cadmium or sulfur solution at different reaction temperatures. These data revealed that the accumulated thickness of the shell after each injection decreased systematically as the reaction temperature decreased. Further, the influence of temperature on the cadmium injections was more pronounced than for the sulfur injections (FIG. 1, top plot). In this aspect, for example, for preparation of the CdSe/CdS core/shell nanocrystals using the methods and precursors disclosed herein, the SILAR shell-growth works well at temperatures from about 220° C. to about 250° C. In another aspect, the CdSe/CdS core/shell nanocrystals underwent SILAR shell-growth from about 220° C. to about 250° C., and in another aspect, from about 235° C. to about 245° C.

Thus, in one aspect, the present invention provides a method for preparing core/shell nanocrystals having the formula $M^1X^1/M^2X^2$, comprising:

a) providing a solution of core nanocrystals of the formula $M^1X^1$;

b) forming a first monolayer of a shell material $M^2X^2$ by contacting the core nanocrystals, in an alternating manner, with a cation ($M^2$) precursor solution in an amount effective to form a monolayer of the cation, and an anion ($X^2$) precursor solution in an amount effective to form a monolayer of the anion; and c) optionally forming subsequent monolayers of shell material $M^2X^2$ by contacting the core/shell nanocrystals, in an alternating manner, with a cation ($M^2$) precursor solution in an amount effective to form a monolayer of the cation, and an anion ($X^2$) precursor solution in an amount effective to form a monolayer of the anion;

wherein $M^1X^1$ comprises a stable, nanometer-sized inorganic solid;

wherein $M^2X^2$ is selected from a II/VI compound or a III/V compound; and wherein $M^1X^1$ and $M^2X^2$ are different. In this aspect, the cation precursor solution can optionally contain at least one ligand, and the anion precursor solution can optionally contain at least one ligand.

In another aspect, the present invention provides a method for preparing core/shell nanocrystals having the formula $M^1X^1/M^2X^2$, comprising:

a) providing a solution of core nanocrystals of the formula $M^1X^1$;

b) forming at least one monolayer of a shell material $M^2X^2$ by contacting the core nanocrystals, in an alternating manner, with a cation ($M^2$) precursor solution in an amount effective to form a monolayer of the cation, and an anion ($X^2$) precursor solution in an amount effective to form a monolayer of the anion;

wherein $M^1X^1$ comprises a stable, nanometer-sized inorganic solid;

wherein $M^2X^2$ is selected from a II/VI compound or a III/V compound; and wherein $M^1X^1$ and $M^2X^2$ are different. Also in this aspect, the cation precursor solution can optionally contain at least one ligand, and the anion precursor solution can optionally contain at least one ligand.

In another aspect, $M^1X^1$ can comprise a II/VI compound or a III/V compound, and in yet another aspect of this invention, $M^1X^1$ and $M^2X^2$ can be independently selected from CdS, CdSe, CdTe, ZnS, ZnSe, ZnTe, HgS, HgSe, HgTe, ZnO, CdO, InP, InAs, GaAs, or GaP.

In still another aspect, this invention provides a composition comprising core/shell nanocrystals, wherein the core material is selected from CdSe, CdS, CdTe, ZnSe, ZnS, ZnTe, HgSe, HgS, HgTe, ZnO, CdO, GaAs, InAs, GaP, or InP;

the shell material is selected from CdSe, CdS, CdTe, ZnSe, ZnS, ZnTe, HgSe, HgS, HgTe, ZnO, CdO, GaAs, InAs, GaP, or InP; and the shell material is different from the core material.

In another aspect of this invention, the SILAR method described herein provides a method whereby the cation ($M^2$) precursor solution can be contacted with the core nanocrystals before the anion ($X^2$) precursor solution can be contacted with the core nanocrystals. In another aspect, the SILAR method described herein provides a method whereby the anion ($X^2$) precursor solution can be contacted with the core nanocrystals before the cation ($M^2$) precursor solution can be contacted with the core nanocrystals.

Yet another aspect of the SILAR method is the further purification of the core/shell nanocrystals.

In still another aspect, the cation precursor solution of this invention can comprise, for example, a metal oxide, a metal halide, a metal nitride, a metal ammonia complex, a metal amine, a metal amide, a metal imide, a metal carboxylate, a metal acetylacetonate, a metal dithiolate, a metal carbonyl, a metal cyanide, a metal isocyanide, a metal nitrile, a metal peroxide, a metal hydroxide, a metal hydride, a metal ether complex, a metal diether complex, a metal triether complex, a metal carbonate, a metal phosphate, a metal nitrate, a metal nitrite, a metal sulfate, a metal alkoxide, a metal siloxide, a metal thiolate, a metal dithiolate, a metal disulfide, a metal carbamate, a metal dialkylcarbamate, a metal pyridine complex, a metal bipyridine complex, a metal phenanthroline complex, a metal terpyridine complex, a metal diamine complex, a metal triamine complex, a metal diimine, a metal pyridine diimine, a metal pyrazolylborate, a metal bis(pyrazolyl)borate, a metal tris(pyrazolyl)borate, a metal nitrosyl, a metal thiocarbamate, a metal diazabutadiene, a metal dithiocarbamate, a metal dialkylacetamide, a metal dialkylformamide, a metal formamidinate, a metal phosphine complex, a metal arsine complex, a metal diphosphine complex, a metal diarsine complex, a metal oxalate, a metal imidazole, a metal pyrazolate, a metal-Schiff base complex, a metal porphyrin, a metal phthalocyanine, a metal subphthalocyanine, a metal picolinate, a metal piperidine complex, a metal pyrazolyl, a metal salicylaldehyde, a metal ethylenediamine, a metal triflate compound, or any combination thereof.

In still another aspect of this invention, for example, the cation precursor solution can comprise, for example, a metal oxide, a metal carbonate, a metal bicarbonate, a metal sulfate, a metal sulfite, a metal phosphate, metal phosphite, a metal halide, a metal carboxylate, a metal hydroxide, a metal alkoxide, a metal thiolate, a metal amide, a metal imide, a metal alkyl, a metal aryl, a metal coordination complex, a metal solvate, a metal salt, or a combination thereof.

Yet another aspect of this invention is a cation precursor solution comprising a ligand selected from a fatty acid, an fatty amine, a phosphine, a phosphine oxide, a phosphonic acid, a phosphinic acid, a sulphonic acid, or any combination thereof, any one of which having up to about 30 carbon atoms. In another aspect, the cation precursor solution comprising a ligand selected from a fatty acid, an fatty amine, a phosphine, a phosphine oxide, a phosphonic acid, a phosphinic acid, a sulphonic acid, or any combination thereof, any one of which having up to about 45 carbon atoms.

Still another aspect of this invention is an anion precursor comprising an element, a covalent compound, an ionic compound, or a combination thereof.

Similarly, in another aspect, this invention provides, for example, a method for preparing core/shell/shell nanocrystals having the formula $M^1X^1/M^2X^2/M^3X^3$ comprising:

a) providing a solution of core nanocrystals of the formula $M^1X^1$;

b) forming at least one monolayer of a first shell material $M^2X^2$ by contacting the core nanocrystals, in an alternating manner, with a first cation ($M^2$) precursor solution in an amount effective to form a monolayer of the first cation, and a first anion ($X^2$) precursor solution in an amount effective to form a monolayer of the first anion; and c) forming at least one monolayer of a second shell material $M^3X^3$ by contacting the core nanocrystals, in an alternating manner, with a second cation ($M^3$) precursor solution in an amount effective to form a monolayer of the second cation, and an second anion ($X^3$) precursor solution in an amount effective to form a monolayer of the first anion;

wherein $M^1X^1$ comprises a stable, nanometer-sized inorganic solid;

wherein $M^2X^2$ and $M^3X^3$ are independently selected from a II/VI compound or a III/V compound; and wherein $M^1X^1$, $M^2X^2$, and $M^3X^3$ are different.

In this aspect, the cation precursors, the cation precursor solutions, the anion precursors, the anion precursor solutions, the ligands, and the like, can comprise those elements, compounds, and materials disclosed herein.

Further, in this aspect, $M^1X^1$ can comprises a II/VI compound or a III/V compound. In yet another aspect of this invention, $M^1X^1$, $M^2X^2$, and $M^3X^3$ can be independently selected from CdS, CdSe, CdTe, ZnS, ZnSe, ZnTe, HgS, HgSe, HgTe, ZnO, CdO, InP, InAs, GaAs, or GaP.

In another aspect of this invention, the SILAR method described herein provides a method whereby the cation ($M^2$) precursor solution is contacted with the core nanocrystals before the anion ($X^2$) precursor solution is contacted with the core nanocrystals. In another aspect, the SILAR method described herein provides a method whereby the anion ($X^2$) precursor solution is contacted with the core nanocrystals before the cation ($M^2$) precursor solution is contacted with the core nanocrystals.

Yet another aspect of the SILAR method is the further purification of the core/shell nanocrystals.

The cation precursors used in the methods disclosed herein can comprise elements or compounds, for example, elements, covalent compounds, or ionic compounds, including but not limited to, oxides, hydroxides, coordination complexes or metal salts, that serve as a source for the electropositive element or elements in the resulting nanocrystal core or shell material. In one aspect of this invention, inexpensive and safe compounds may be used as cation precursors. Anion precursors can also comprise elements, covalent compounds, or ionic compounds that serve as a source for the electronegative element or elements in the resulting nanocrystal. In one aspect of this invention, inexpensive and safe elements or compounds may be used as anion precursors, such as naturally occurring substances. These definitions anticipate that ternary compounds, quaternary compounds, and even more complex species may be prepared using the methods disclosed herein, in which case more than one cation precursor, more than one anion precursor, or both, may be used. When dual or multiple cation elements were used in the growth of a given monolayer, the resulting nanocrystals were cation-doped at the given monolayer if the other part of the nanocrystals contained only a single cation. The same method can be used for the preparation of anion-doped nanocrystals.

In one aspect of this invention, the methods disclosed herein are applicable to core/shell nanocrystals prepared using a range of cation precursor compounds for the core and the shell material, for example, precursors of the group II metals (for example, Zn, Cd, or Hg), the group III metals (for example, Al, Ga, or In), the group IV metals (for example, Ge, Sn or Pb), or the transition metals (including, but not limited to, Ti, Zr, Hf, V, Nb, Ta, Cr, Mo, W, Mn, Tc, Re, Fe, Ru, Os, Co, Rh, Ir, Ni, Pd, Pt, Cu, Ag, Au, and the like). (See, F. A. Cotton et al., Advanced Inorganic Chemistry, 6th Edition, (1999).) The cation precursor for the core and the shell material can constitute a wide range of substances, including, but not limited to, a metal oxide, a metal hydroxide, a metal carbonate, a metal bicarbonate, a metal sulfate, a metal sulfite, a metal phosphate, metal phosphite, a metal halide, a metal carboxylate, a metal alkoxide, a metal thiolate, a metal amide, a metal imide, a metal alkyl, a metal aryl, a metal coordination complex, a metal solvate, a metal salt, and the like.

In another aspect, ligands, sometimes used for cation precursors, may be selected from a range of compounds including, but not limited to, fatty acids, fatty amines, phosphines, phosphine oxides, phosphonic acids, phosphinic acids, sulphonic acids, or any combination thereof. A range of anion precursors for the core and the shell material may also be used, including, but not limited to, the element itself (oxidation state 0), covalent compounds, or ionic compounds.

To examine the stability of the core CdSe nanocrystals, the UV-Vis absorption spectrum of these nanocrystals was examined after heating at 240° C. for at least 30 minutes, without injecting any solution of shell materials. The UV-Vis absorption spectrum of the core CdSe nanocrystals showed no noticeable change as a result of this heat treatment. The PL QY of the CdSe core nanocrystals increased in the first 5-15 minutes of this heat treatment, (see: Talapin, D.; Rogach, A. L.; Kornowski, A.; Haase, M.; Weller, H. *Nano Lett.* 2001, 1, 207, which is incorporated herein by reference in its entirety) and often decreased after the initial heating period at 240° C. Higher temperatures, for example 260° C. and above, made it difficult to prevent Ostwald ripening of the core and core/shell nanocrystals. Therefore, except where indicated, the data described herein were obtained using shell growth reactions at abut 240° C.

FIG. 1 (middle plot) illustrates a spectral comparison of the CdSe/CdS core/shell nanocrystals with the same shell thickness, grown onto the same batch of core nanocrystals under different temperatures. While not intending to be bound by theory, this comparison suggests that as the temperature decreases, increasingly less of the cation precursor (in this example, cadmium) and anion precursor (in this example, sulfur) injected into the solution grow onto the surface of the existing nanocrystals, but instead begin to form isolated CdS nanocrystals through homogeneous nucleation process. Thus, relative to the absorbance at the first absorption peak, the absorbance in the wavelength range below 500 nm for the low temperature reactions increased rapidly, indicating the formation of individual CdS nanocrystals.

In those cases where isolated CdS nanocrystals formed in the growth process, they could be separated readily from the CdSe/CdS core/shell nanocrystals, either by extraction or by precipitation. In one aspect, extraction purification could be carried out by extracting the pure CdS nanocrystals into the methanol layer from the hexanes/ODE layer containing CdSe/CdS core/shell nanocrystals. Under UV irradiation, the methanol layer emitted blue, and the hexanes/ODE layer exhibited the PL of the core/shell nanocrystals. After purification, the PLE (photoluminescence excitation) spectra of the core/shell nanocrystals were changed dramatically (FIG. 1, bottom plot). As shown in FIG. 1 (bottom plot), the existence of isolated CdS particles in the solution often caused a significant drop of the PLE below 500 nm, which is likely due to the absorption of isolated CdS nanocrystals in that optical window.

Figure 2:
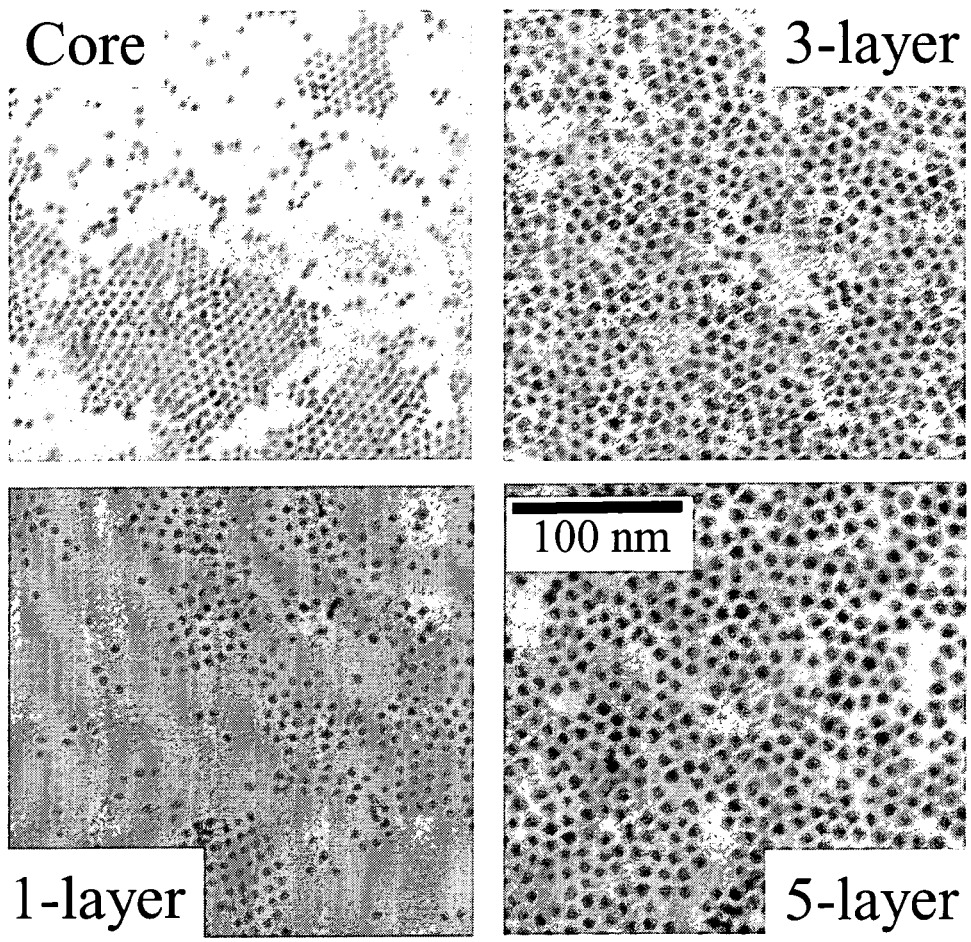
FIG. 2 provides TEM (transmission electron microscopy) images of CdSe plain core nanocrystals and the corresponding core/shell nanocrystals with different shell thickness from the same SILAR reaction.

The size, shape and size/shape distribution of the CdSe/CdS core/shell nanocrystals were controlled using SILAR. FIG. 2 exhibits four TEM images of CdSe plain core nanocrystals and the corresponding core/shell nanocrystals with different shell thicknesses. The size increase observed by TEM correlated well with the numbers of CdS monolayers estimated from the injections. The nearly monodisperse core nanocrystals formed well-developed, two-dimensional (2D) superlattices of the nanocrystals. Upon the growth of CdS shell, 2D superlattice was still readily observed if the shell thickness was one or two monolayers of CdS. Core/shell nanocrystals with three or more monolayers of CdS were mostly ordered locally.

As indicated in FIG. 2, in one aspect of this invention, the shape of the core/shell nanocrystals appeared to depend on the shell thickness (FIG. 2). Nanocrystals with thin shells, for example one or two monolayers, maintained the dotted shape of the core nanocrystals, and thus readily formed 2D superlattices. Nanocrystals with thicker shells were observed to have somewhat elongated shapes, and 2D superlattices did not form if those nanocrystals were randomly oriented, which occurred at low particle concentrations. Thus, orientation of those elongated core/shell nanocrystals was achieved by depositing them from a relatively concentrated solution. Accordingly, as shown in FIG. 3, this method made it possible to obtain superlattice packing with thousands of nanocrystals.

Figure 3:
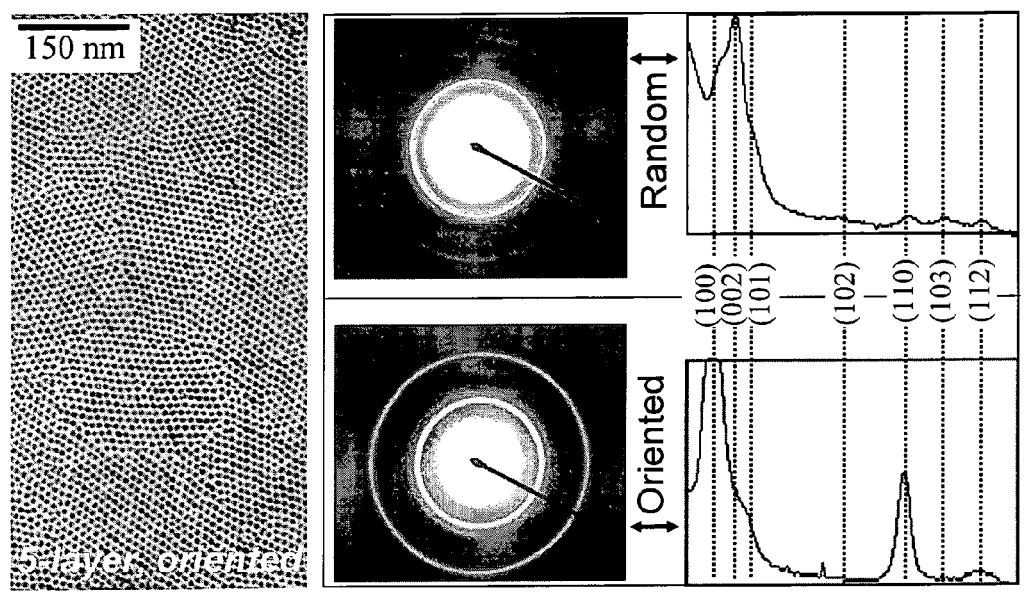
FIG. 3 illustrates core/shell nanocrystals with a relatively thick CdS shell, five monolayers in this case, formed superlattice only if the particle concentration of the deposition solution was high (left). The selected area electron diffraction (SAED) patterns and the corresponding diffraction intensity profiles of randomly deposited (top raw) and oriented (bottom raw) core/shell nanocrystals.
Figure 4:
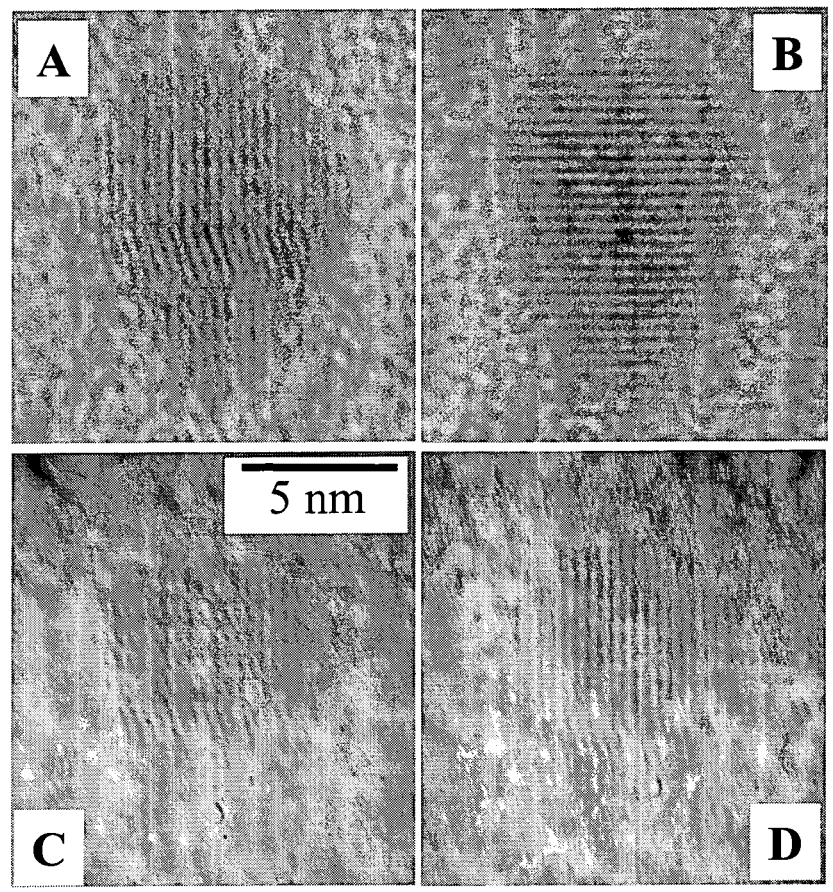
FIG. 4 demonstrates HRTEM (high resolution transmission electron microscopy) images of four representative core/shell nanocrystals, each having a 3.5 nm CdSe core with five monolayers of CdS shell material overcoating the CdSe core.

The appearance of almost all nanocrystals in the superlattice shown in FIG. 3 was dot-shaped. This observation reflects that the nanocrystals had oriented themselves on the grids with their long axis perpendicular to the substrate. The selected area electron diffraction (SAED) patterns shown in FIG. 3 further revealed that the c-axis of the nanocrystals in the superlattice was perpendicular to the substrate. These two observations suggested that the long axis of the core/shell nanocrystals with relatively thick shells was the c-axis of the wrutzite structure, which was verified by High-resolution TEM measurements. As shown in FIG. 4 (A and B), the shape of the 5-layer nanocrystals was significantly elongated along the c-axis, and approached a petal-shape. The dimension along the c-axis of the top two nanocrystals in FIG. 4 is about 9 nm, while the dimension perpendicular to the c-axis is about 7 nm. A small portion of the core/shell nanocrystals with 5-layer CdS were found to more closely resemble a dot-shape (for example, see bottom two images in FIG. 4). Thus, overall, the distribution of the aspect ratio of the core/shell nanocrystals with thick shells was not as narrow as that of the dimension of the short axis.

In one aspect of this invention, although 5-layer CdS is illustrated in the Figures provided herein, the core/shell nanocrystals of this invention could be characterized by a thickness of the shell material from 1 to about 15 monolayers. Thus, in this aspect of the invention, the thickness of any shell material could be 1, 2, 3, 4, 5, 6, 7, 8, 9, 10, 11, 12, 13, 14, 15, or more monolayers.

Figure 5:
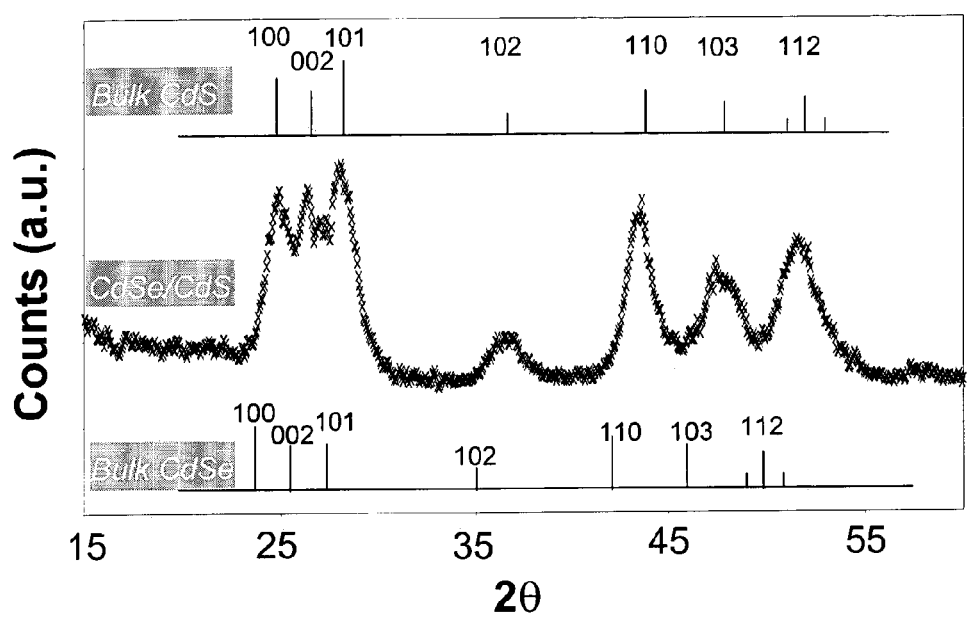
FIG. 5 presents the XRD (X-ray diffraction) pattern of CdSe/CdS core/shell nanocrystals having a 3.5 nm CdSe core with five monolayers of CdS shell material overcoating the CdSe core. For comparison, the standard powder diffraction patterns of wurtzite CdSe and CdS bulk crystals are provided.

For the CdSe/CdS core/shell nanocrystals illustrated in the Figures, the X-ray diffraction patterns of the core/shell nanocrystals shifted from a wurtzite CdSe-like pattern to a wurtzite CdS-like pattern as the shell thickness increased upon successive CdS shell layering. For the core/shell nanocrystals with five monolayers of CdS shell, the diffraction pattern was substantially the same as pure CdS nanocrystals of the same size, as illustrated in FIG. 5. The crystal domain size calculated using the Sherrer Equation using the (110) peak is about 7 nm, which is consistent with the TEM results discussed above. The composition of a thick shell CdSe/CdS core/shell nanocrystal with five monolayers of CdS shell, is approximately 10:1 molar ratio of CdS:CdSe. The relatively low intensity and broad peak of the (103) peak in comparison to the (110) peaks in the diffraction pattern shown in FIG. 5 are consistent with the existing stacking faults perpendicular to the c-axis observed by High Resolution TEM (HRTEM) as seen in FIG. 4, with one stacking fault per particle in average. (See: Murray, C. B.; Norris, D. J.; Bawendi, M. G. *J. Am. Chem. Soc.* 1993, 115, 8706-8715.)

Figure 6:
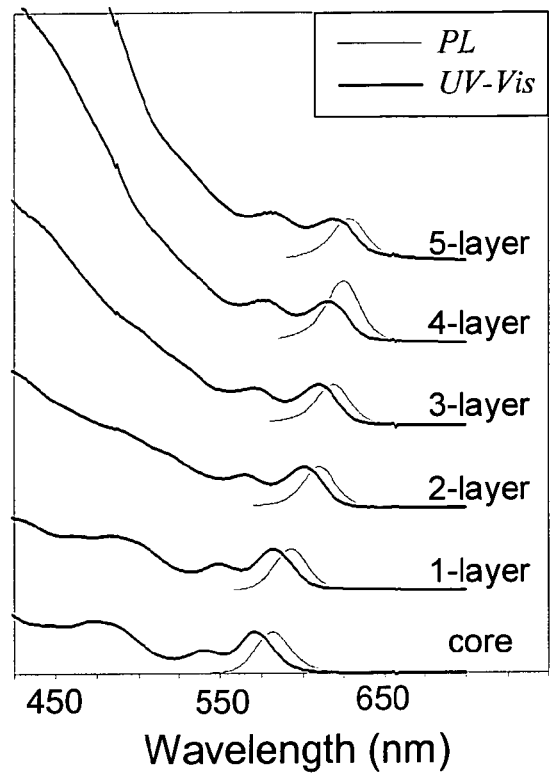
FIG. 6 illustrates the following. Left: the evolution of the UV-Vis and PL (photoluminescence) spectra of the CdSe/CdS core/shell nanocrystals upon the growth of the CdS shell in a typical reaction. Right: Asymmetric PL spectra of CdSe/CdS core/shell nanocrystals with five monolayers of CdS shell overcoating the CdSe core.
Figure 6:
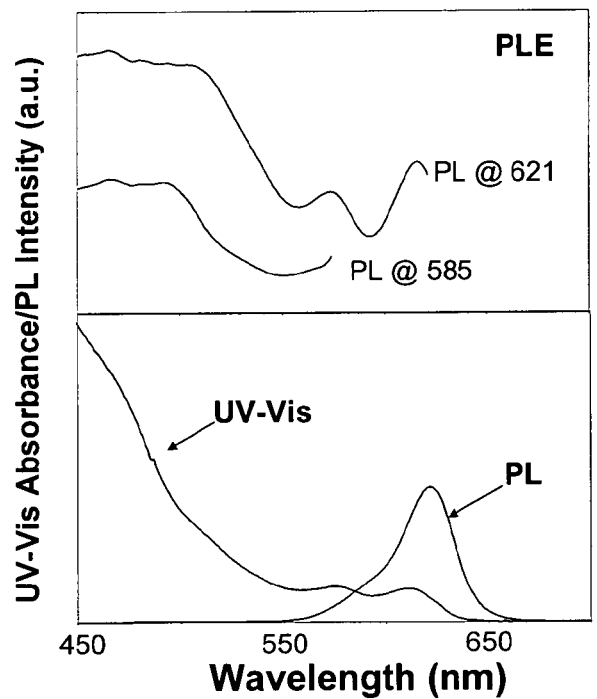

In another aspect of this invention, for example, the UV-Vis and PL spectra of the core/shell nanocrystals of a typical reaction are illustrated in FIG. 6 (left panel). The sharp features of the absorption spectra and the narrow PL peaks are consistent with the narrow size distribution of the core/shell nanocrystals shown in FIGS. 2 and 3.

In yet another aspect, for example, the PL spectrum of core/shell nanocrystals with thick shells often possessed a shoulder on the high energy side, and the relative intensity of this shoulder increased by purifying the nanocrystals by removing traces of the side products and initial reactants, by the methods described in the Examples. The photoluminescence excitation, PLE, of the shoulder emission was approximately the same to that of the band edge PL (FIG. 6, right panel).

Figure 7:
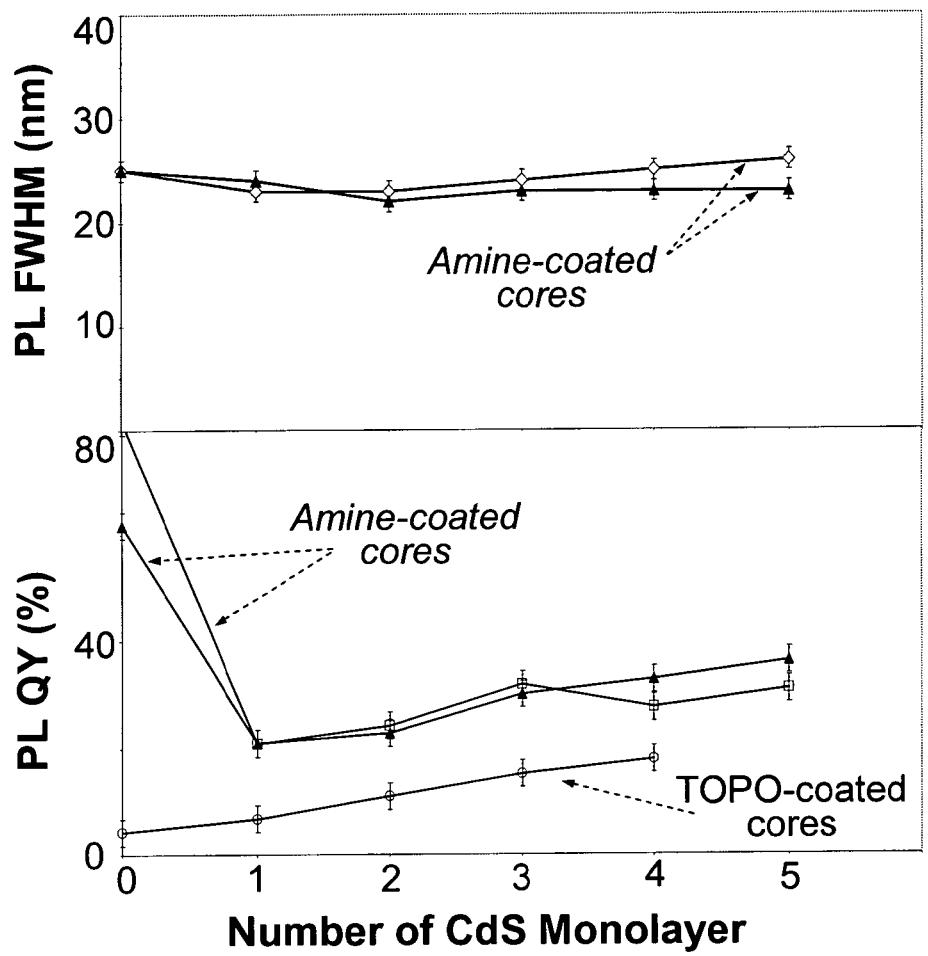
FIG. 7 plots the PL QY (photoluminescence quantum yield) and PL FWHM (photoluminescence emission line full-width at half-maximum intensity) of the as-prepared CdSe/CdS core/shell nanocrystals plotted relative to the number of CdS monolayers overcoating the CdSe core.

For the CdSe/CdS core/shell nanocrystals used to illustrate the SILAR method, the photoluminescence quantum yields (PL QY) and photoluminescence Full-Width-at-Half-Maximum peak width (PL FWHM) of the core/shell nanocrystals vary as a function of shell thickness of the core/shell nanocrystals, as follows. The PL QY of the core/shell nanocrystals was observed to increase as the shell thickness increased, as shown in FIG. 7. Additionally, the PL QY of the plain core nanocrystals prior to the shell growth also varied significantly even if the reactions were carried out with the same batch of the core nanocrystals as shown in FIG. 7. However, with the same batch of nanocrystal cores, the peak positions, the PL QY, and the PL FWHM of the core/shell nanocrystals generated by two parallel reactions were similar (FIG. 7).

In another aspect, growth reactions with TOPO-coated nanocrystal cores generated core/shell nanocrystals with significantly lower PL QY in comparison to the ones with amine-coated cores, although a systematic increase of the PL QY was also observed upon the increase of the shell thickness (FIG. 7).

In one aspect, the photoluminescence Full-Width-at-Half-Maximum peak width (PL FWHM) of the core/shell nanocrystals maintained the original value of the original cores within experimental error (FIG. 7, top). This observation is consistent with the good control of the size distribution of the core/shell nanocrystals described above. However, the PL spectra of the core/shell nanocrystals with thicker shells, for example at least about five monolayers, often possessed a tail spectroscopic feature on the high energy side as described above.

Multigram-scale growth of the core/shell nanocrystals was also achieved using the SILAR method disclosed herein. The quality of the resulting nanocrystals was similar to those obtained from small scale syntheses. The TEM images shown in FIGS. 2 and 3 were all recorded with the nanocrystals generated by a large scale synthesis which yielded about 2.5 grams core/shell nanocrystals, and are representative of those obtained from small scale syntheses as well. In one aspect, even for this large scale synthesis, dropwise addition of the precursor solutions was not necessary to obtain high quality nanocrystals.

Figure 10:
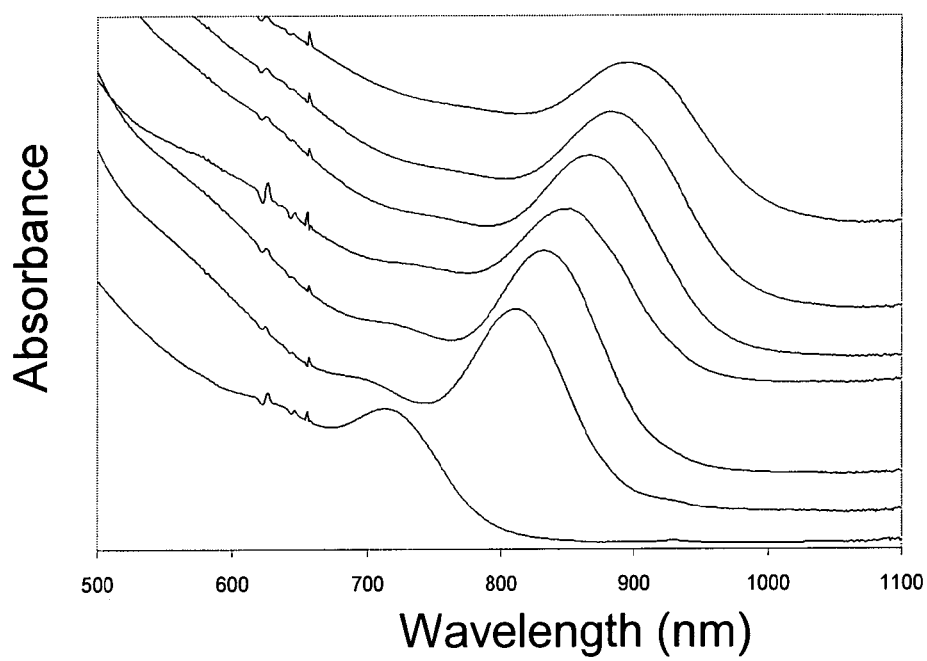
FIG. 10 presents a plot of the temporal evolution of UV-Vis of InAs/CdSe core/shell nanocrystals, illustrating, among other things, how the growth of the CdSe shell layers shifted the UV-Vis peak of the original InAs plain core nanocrystals significantly.
Figure 11:
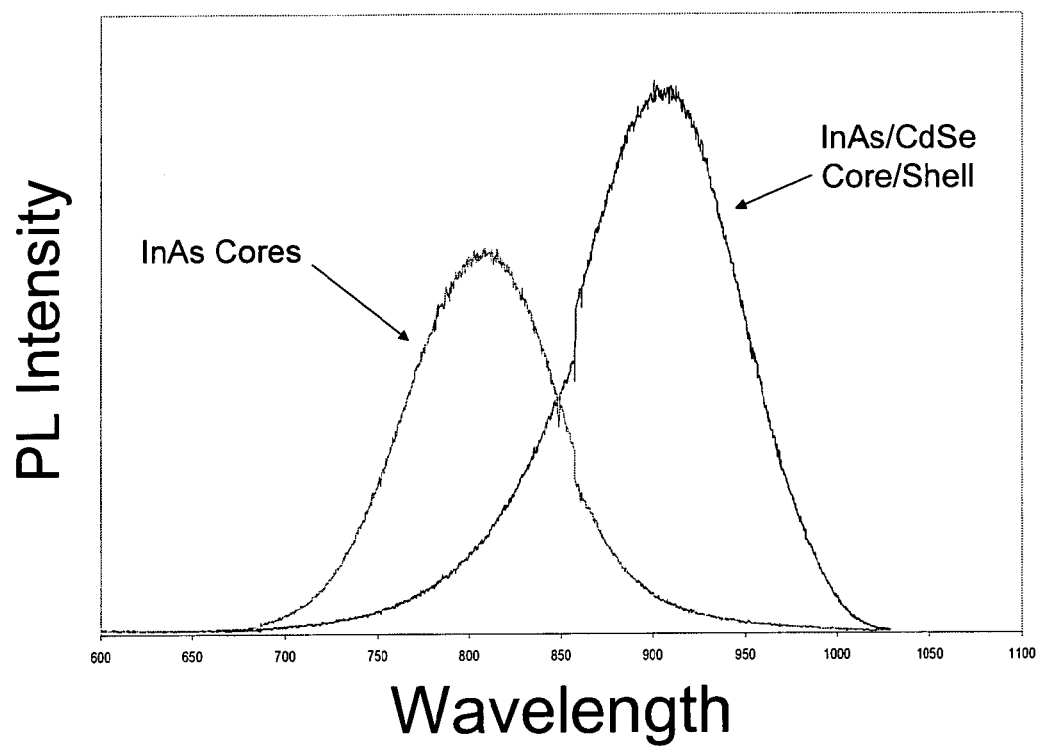
FIG. 11 presents a plot of the PL spectra of InAs and InAs/CdSe core/shell nanocrystals, illustrating, among other things, how the growth of the CdSe shell layers enhanced the photoluminescence of the InAs plain core nanocrystals significantly.

The Successive ionic layer adsorption and reaction (SI-LAR) method is also applicable to many other semiconductor core/shell nanocrystals. In one aspect, for example, high quality core/shell nanocrystals that can be prepared by the SILAR method disclosed herein include, but are not limited to, CdSe/CdS, CdSe/ZnSe, CdSe/ZnS, CdS/ZnS, CdTe/CdSe, CdTe/CdS, CdTe/ZnTe, CdTe/ZnSe, CdTe/ZnS, ZnSe/ZnS, ZnTe/CdS, ZnTe/ZnSe, InAs/InP, InAs/CdSe, InAs/CdS, InAs/ZnS, InP/CdS, InP/ZnS, InP/ZnSe, InAs/InP/CdS, CdS/CdSe, CdS/InP, and the like. Moreover, the optical properties and quality of core/shell nanocrystals prepared by the SILAR method are often improved over those prepared by traditional methods. For example, InAs/InP core shell nanocrystals prepared using traditional approaches are reported to exhibit PL QY values lower than the plain core InAs nanocrystals (see: Cao, Y.; Banin, U. *J. Am. Chem. Soc.* 2000, 122, 9692-9702). However, the core/shell nanocrystals with III-V semiconductor nanocrystals as the cores and synthesized using SILAR technology encompassed by this invention, all possessed higher PL QY and better stability against photo-oxidation than the corresponding plain core nanocrystals did. For example, using. ZnSe and ZnS as the shell materials, it was observed that the PL QY of highly luminescent CdSe core nanocrystals could be maintained at above 50% level. Thus, CdSe/ZnSe and CdSe/ZnS core/shell nanocrystals may be brighter emitting materials than the CdSe/CdS system. The last two core/shell systems, CdS/CdSe and CdS/InP, represent a new series of colloidal quantum structures, quantum shells. Specific examples of the growth of core/shell nanocrystals using III-V semiconductor nanocrystals as the cores are illustrated in FIGS. 10 and 11.

Figure 8:
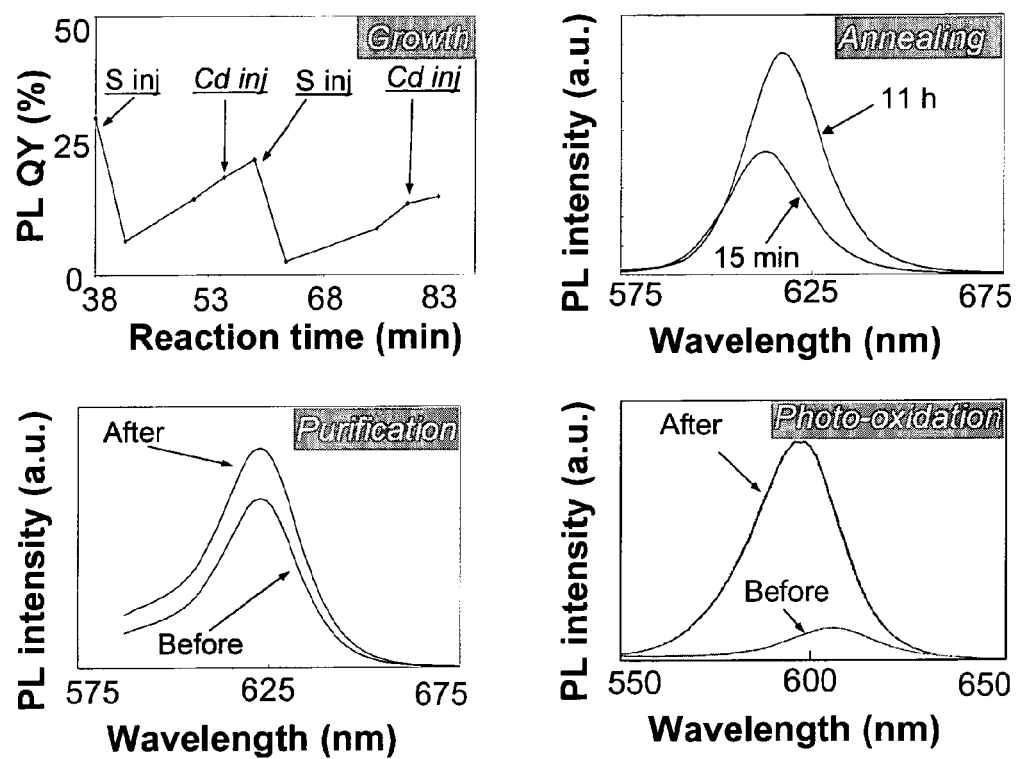
FIG. 8 demonstrates the PL darkening and brightening phenomena observed in the growth and manipulation of CdSe/CdS core/shell nanocrystals.

In one aspect, darkening and brightening phenomena were observed in the preparation of the core/shell nanocrystals of the present invention, as illustrated in FIG. 8. In the growth process, especially for those reactions that occurred at relatively low temperatures, a darkening process was observed immediately after each injection of the sulfur stock solution. When this darkening was observed, a rapid increase of the shell thickness, as indicated by a rapid red shift of the absorption peak, was typically observed. In the case of the CdSe/CdS core/shell nanocrystals, annealing sometimes resulted in a brightening phenomenon, thus-improved the PL QY of these nanocrystals, accompanied by a small red-shift of the emission peak (see FIG. 8).

Figure 9:
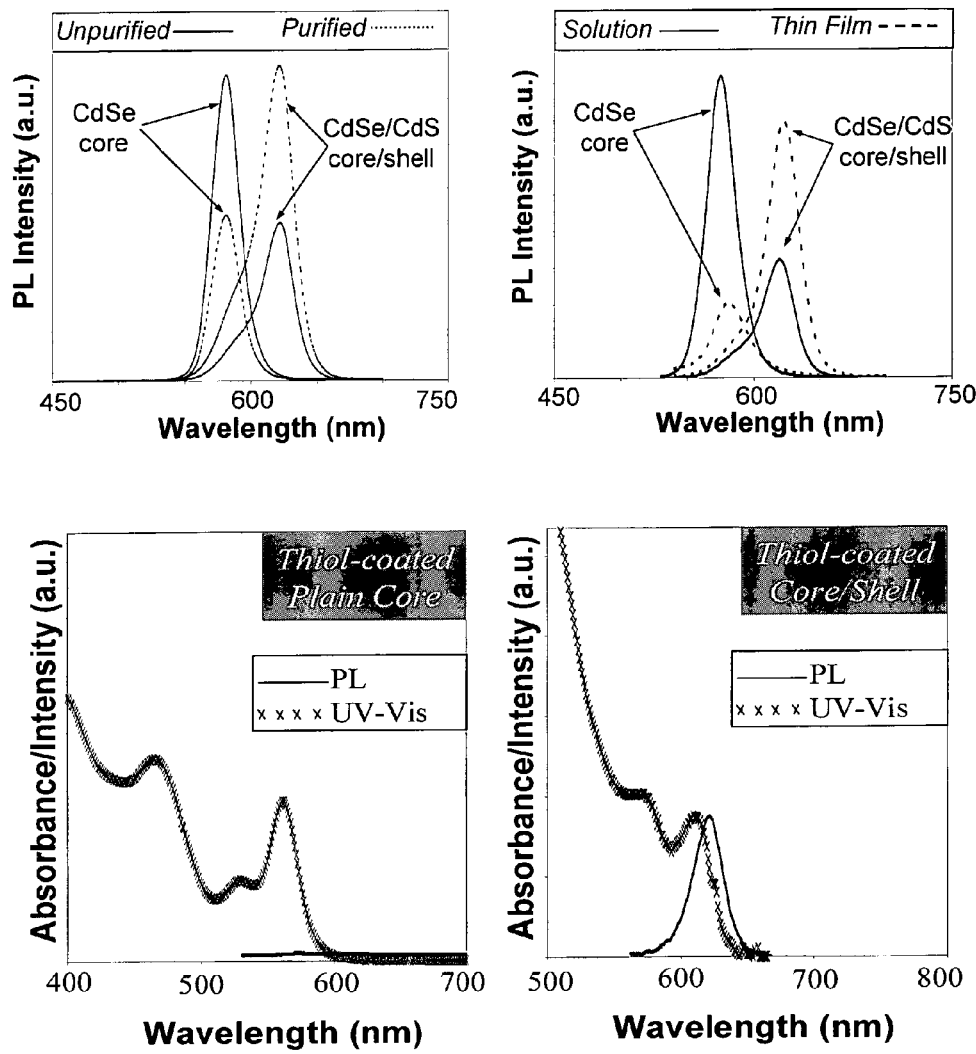
FIG. 9 presents a comparison of the processability of plain core and core/shell nanocrystals. Top-right: PL spectra of CdSe plain core and CdSe/CdS core/shell nanocrystals, before and after purification by the precipitation/decantation procedure. Top-left: PL spectra of the CdSe plain core and CdSe/CdS core/shell nanocrystals upon the deposition of the nanocrystals onto substrates. Bottom: UV-Vis and PL spectra of plain core and core/shell nanocrystals coated with hydrophilic thiols.

The CdSe/CdS core/shell nanocrystals described herein could be brightened by laser photo-irradiation when oxygen was present in the solution. Brightening was always accompanied by a noticeable blue shift of the absorption/PL spectrum, suggesting the size of the semiconductor nanocrystals decreased. While not intending to be bound by this theory, these results imply that the photo-induced brightening phenomenon observed here is due to the photo-oxidation of the shell material. The rate of this photo-oxidation of core/shell nanocrystals was strongly dependent on the environment, although it occurred in a much slower rate in comparison to the corresponding plain core nanocrystals. In water or polar solvents, photo-oxidation of hydrophilic thiol-coated CdSe/shell nanocrystals occurred easily, as illustrated in FIG. 9. In non-polar solvents, the oxidation of the ODA-coated core/shell nanocrystals required from hours to days to show a noticeable change. When the core/shell nanocrystals were embedded in thin polymer film, no photo-oxidation was observed in air with intense laser radiation for at least 1-2 hours. It was observed that those core/shell nanocrystals embedded in thin polymer film did not blink as frequently as the corresponding core nanocrystals, with most nanocrystals existing at "on" state for most of the time.

In another aspect of this invention, a brightening phenomenon was observed when the nanocrystals were purified using either the extraction or precipitation method. The PL QY of the core/shell nanocrystals increased by the removal of the side products and unreacted precursors (see FIG. 8), although the emission peak retained the same position after purification. The shoulder at the high energy side of the PL spectrum of the core/shell nanocrystals with a thick shell often became more obvious after purification (FIG. 8).

The processability of the core/shell nanocrystals was superior to that of the corresponding core nanocrystals, as illustrated in FIG. 9. Thus, the PL QY of core/shell nanocrystals increased by purification procedures through either precipitation or extraction. However, the highly luminescent CdSe core nanocrystals became barely emitting after a parallel precipitation procedure. In one aspect of this invention, in the case of the plain core nanocrystals, in order to maintain a reasonable PL brightness, the purification processing is typically stopped when there is still a significant amount of free amine in the solution along with the plain core nanocrystals.

The presence of free amine in the solution is know to adversely affect the PL emission efficiency of plain core nanocrystals when deposited as thin films for LEDs, lasers, and the like, as the films tend to become opaque. In contrast, purified core/shell nanocrystals formed optically clear thin films using the same procedures. Furthermore, even though the core/shell nanocrystals in solution were often less bright than the plain core nanocrystals dissolved in the same solvent, they possessed higher PL QY than the plain core nanocrystals did when both types of nanocrystals were in the form of solid films, as illustrated in FIG. 9.

In one aspect of this invention, one typical method to convert hydrophobic semiconductor nanocrystals into water soluble semiconductor nanocrystals, for bio-medical applications and the like, is to replace the original hydrophilic ligands by hydrophilic thiol ligands. (See, for example: Bruchez, M.; Moronne, M.; Gin, P.; Weiss, S.; Alivisatos, A. P. *Science* 1998, 281, 2013-2016; Chan, W. C. W.; Nie, S. M. *Science* 1998, 281, 2016-2018; Mattoussi, H.; Mauro, J. M.; Goldman, E. R.; Anderson, G. P.; Sundar, V. C.; Mikulec, F. V.; Bawendi, M. G. *J. Am. Chem. Soc.* 2000, 122, 12142.) Highly emitting, plain core nanocrystals became not emitting at all after the amine ligands were replaced by hydrophilic thiols, as shown in FIG. 9. In contrast, the PL of core/shell nanocrystals remained to some extent after the same treatment with hydrophilic thiols. Furthermore, the PL brightness of the thiol-coated core/shell CdSe/CdS nanocrystals can be recovered by the controlled photo-chemical (as illustrated in FIG. 8) or chemical oxidations. However, the same oxidation treatments usually decomposed the plain core CdSe nanocrystals rapidly, without any noticeable recovery of the photoluminescence. These results suggest that the CdSe/CdS core/shell nanocrystals are substantially more stable than the corresponding plain core nanocrystals under certain harsh chemical and thermal processing conditions.

The epitaxial growth feature of the resulting nanocrystals could be determined using the criteria established previously, as described in Peng, X.; Schlamp, M. C.; Kadavanich, A. V.; Alivisatos, A. P. *J. Am. Chem. Soc.* 1997, 119, 7019-7029, which is incorporated herein in its entirety by reference. The immediate and significant red-shift of the absorption spectra upon the growth of each monolayer of CdS (illustrated in FIGS. 1 and 6) revealed that the resulting nanocrystals are core/shell structures, instead of alloy particles. The TEM and XRD measurements (see FIGS. 4 and 5) indicated that the core/shell nanocrystals are single crystals. The lattice fringes including the stacking faults (FIG. 4) of each nanocrystal extended completely across each nanocrystal, which is a hallmark of epitaxial growth.

Thus, in one aspect, the present invention provides core/shell nanocrystals, and a composition comprising core/shell nanocrystals, wherein:

the nanocrystals comprise a core material and a shell material overcoating the core material, each of which is independently selected from a II/VI compound or a III/V compound, the band gap of the core material is less than the band gap of the shell material; and the thickness of the shell material is from 1 to about 15 monolayers.

Thus, in this aspect of the invention, the thickness of the shell material could be 1, 2, 3, 4, 5, 6, 7, 8, 9, 10, 11, 12, 13, 14, 15, or more monolayers, and still maintain the monodispersity of the core/shell nanocrystals.

In another aspect, the core/shell nanocrystals of this invention may exhibit a type-I band offset or a type-II band offset. Further, and in another aspect, examples of the core/shell nanocrystals of this invention include, but are not limited to, CdSe/CdS, CdSe/ZnSe, CdSe/ZnS, CdS/ZnS, CdTe/CdSe, CdTe/CdS, CdTe/ZnTe, CdTe/ZnSe, CdTe/ZnS, ZnSe/ZnS, ZnTe/CdS, ZnTe/ZnSe, InAs/InP, InAs/CdSe, InAs/CdS, InAs/ZnS, InP/CdS, InP/ZnS, InP/ZnSe, InAs/InP/CdS, CdS/CdSe, CdS/InP, or a mixture thereof.

In still another aspect, the as-prepared core/shell nanocrystals can exhibit a photoluminescence quantum yield (PL QY) up to about 40%. In another aspect, the core/shell nanocrystals can photoluminesce at a wavelength from about 400 to about 1000 nm. In yet another aspect, the core/shell nanocrystals can exhibit a photoluminescence emission line characterized by a FWHM of about 60 nm or less, about 55 nm or less, about 50 nm or less, about 45 nm or less, about 40 nm or less, about 35 nm or less, about 30 nm or less, about 28 nm or less, or about 25 nm or less.

In another aspect, the core/shell nanocrystals of this invention are monodisperse. In this aspect, the core/shell nanocrystals can be characterized by a size distribution having a standard deviation no greater than about 15% of a mean diameter of the population of core/shell nanocrystals, no greater than about 12% of a mean diameter of the population of core/shell nanocrystals, no greater than about 10% of a mean diameter of the population of core/shell nanocrystals, no greater than about 7% of a mean diameter of the population of core/shell nanocrystals, or no greater than about 5% of a mean diameter of the population of core/shell nanocrystals.

In another aspect, this invention provides devices comprising the core/shell nanocrystals and compositions of this invention, including, but not limited to, light-emitting diodes, biological labeling agents, photoelectric devices, solar cells, lasers, and the like.

In yet another aspect, this invention provides a population of nanocrystals comprising a plurality of nanocrystals, wherein:

each nanocrystal comprises a core material and the shell material overcoating the core material, each of which is independently selected from a II/VI compound or a III/V compound, wherein the band gap of the core material is less than the band gap of the shell material;

wherein the population of nanocrystals is substantially monodisperse; and wherein the plurality of nanocrystals exhibit a photoluminescence quantum yield (PL QY) of greater than or equal to about 20%.

In this aspect, for example, the core material can be selected from CdSe, CdS, InAs, or InP; the shell material can be selected from CdS, CdSe, ZnSe, ZnS, or InP; and the shell material is different from the core material.

Also in this aspect, the plurality of nanocrystals can exhibit a photoluminescence quantum yield (PL QY) of greater than or equal to about 5%, greater than or equal to about 10%, greater than or equal to about 20%, greater than or equal to about 30%, greater than or equal to about 40%, greater than or equal to about 50%, greater than or equal to about 60%, or greater than or equal to about 70%.

In yet another aspect, this invention provides a population of core/shell nanocrystals, wherein:

the core material is selected from CdSe, CdS, CdTe, ZnSe, ZnS, ZnTe, HgSe, HgS, HgTe, ZnO, CdO, GaAs, InAs, GaP, or InP;

the shell material is selected from CdSe, CdS, CdTe, ZnSe, ZnS, ZnTe, HgSe, HgS, HgTe, ZnO, CdO, GaAs, InAs, GaP, or InP; and the shell material is different from the core material.

In another aspect, the plurality of nanocrystals of this invention are substantially monodisperse. In this aspect, the plurality of nanocrystals can be characterized by a size distribution having a standard deviation no greater than about 15% of a mean diameter of the population, no greater than about 12% of a mean diameter of the population, no greater than about 10% of a mean diameter of the population, no greater than about 7% of a mean diameter of the population, or no greater than about 5% of a mean diameter of the population.

In still another aspect, the plurality of nanocrystals can exhibit a photoluminescence quantum yield (PL QY) from about 20% to about 40%. In another aspect, the plurality of nanocrystals can photoluminesce at a wavelength from about 400 to about 1000 nm. In yet another aspect, the plurality of nanocrystals can exhibit a photoluminescence emission line characterized by a FWHM of about 60 nm or less, about 55 nm or less, about 50 nm or less, about 45 nm or less, about 40 nm or less, about 35 nm or less, about 30 nm or less, about 28 nm or less, or about 25 nm or less.

Theoretical Considerations

While not intending to be bound by the following theory, it is believed that the properties of the CdSe/CdS core/shell system produced by SILAR technology can be explained as follows. The photo-generated excitons in the CdSe/CdS core/shell system are delocalized in both core and shell materials, with holes mostly confined in the core and electrons delocalized in both core and shell. (See: Peng, X.; Schlamp, M. C.; Kadavanich, A. V.; Alivisatos, A. P. *J. Am. Chem. Soc.* 1997, 119, 7019-7029.) The delocalization of the excitons fosters the shell-thickness dependent optical properties of CdSe/CdS core/shell system, which provides us convenient probes to study the growth of core/shell nanocrystals. However, the poor overlap of the wavefunctions of the photo-generated hole and electron makes CdSe/CdS core/shell nanocrystals not emit as well as CdSe/ZnS or CdSe/ZnSe core/shell nanocrystals, as observed. In one aspect, for example, the PL QY of the as-prepared CdSe/ZnSe and CdSe/ZnS nanocrystals synthesized using SILAR could reach above 50%. In molecular beam epitaxy-grown (MBE-grown) quantum wells of CdSe—CdS system, the poor overlap of the hole and electron of excitons was found to induce so-called spatially indirect PL (photoluminescence), with the hole mostly in the CdSe and the electron mostly in CdS layer. (See, for example: Langbein, W.; Hetterich, M.; Gruen, M.; Klingshirn, C.; Kalt, H. *Appl. Phys. Lett.* 1994, 65, 2466-68, which is incorporated herein by reference in its entirety.) Again, while not intending to be bound by theory, the high energy shoulder observed for CdSe/CdS core/shell nanocrystals with a thick shell is likely due to such spatially indirect PL. As shown in FIG. 6 (right), although the shoulder was about 35 nm separated from the emission peak, the PLE spectra of the two emission features were quite similar. This observation likely indicates that the shoulder in the PL spectrum should not be due to either the emission from isolated CdS nanocrystals or the emission of another set of sizes. As illustrated in FIG. 8, purification often increased the relative PL intensity of the shoulder emission in comparison to that of the peak itself. This characteristic suggests that the shoulder emission may possess more of a surface feature, which is consistent with the delocalization of the hole into the CdS shell layer required for the spatially indirect emission. This interesting PL property of CdSe/CdS system was likely not observed previously because of the less controlled growth, which made it difficult to grow thick CdS shells.

The photoluminescence (PL) properties of highly crystalline semiconductor nanocrystals are strongly dependent on the surface of the nanocrystals. This dependence also applies to the CdSe/CdS core/shell nanocrystals due to the significant delocalization of the excitons in this system as discussed herein. Again, while not intending to be bound by theory, the brightening and darkening phenomena shown in FIG. 8 are all probably related to the improvement of the surface structure and surface environment of the nanocrystals. The darkening phenomenon observed right after the introduction of the sulfur precursors is consistent with the accompanied rapid growth of the core/shell nanocrystals since a rapid growth often causes the disorder of the surface of nanocrystals. (See, for example: Qu, L; Peng, X. *J. Am. Chem. Soc.* 2002, 124, 2049-2055; Talapin, D. V.; Rogach, A. L.; Shevchenko, E. V.; Kornowski, A.; Haase, M.; Weller, H. *J. Am. Chem. Soc.* 2002, 124, 5782-5790, which is incorporated herein by reference in its entirety.) A similar explanation can be applied to the brightening observed upon annealing. The improvement of emission properties of the core/shell nanocrystals by purification is possibly related to the removal of some critical impurities in the growth solution which quenches the PL of the core/shell nanocrystals.

In one aspect, photo-oxidation and chemical oxidation was observed to improve the PL QY of CdSe/CdS core/shell nanocrystals significantly although it typically does not improve the PL brightness of plain core CdSe nanocrystals. While not intending to be bound by theory, one possible reason is that the bond length of Cd—O bond is much smaller than that of the Cd—Se bond. As a result, the CdO formed by oxidation might not stay on the surface of the remaining CdSe nanocrystal cores. In comparison, the Cd—S bond length is about 5-6% shorter than that of the Cd—Se bond. Therefore, a thin layer of CdO might adhere to the surface of the remaining core/shell nanocrystals, resulting in a CdSe/CdS/CdO complex structure. Thus, it is possible that the extra CdO shell could further provide electronic passivation for the CdSe cores. Thus, if the above mechanism is correct, oxidation of core/shell nanocrystals with ZnS or ZnSe shell should also improve their PL QY. However, since the absorption and PL peak positions of CdSe/ZnS and CdSe/ZnSe core/shell nanocrystals are nearly insensitive to the shell thickness of the nanocrystals, it is difficult to distinguish the influence of photo-oxidation from other factors, such as photo-annealing.

This invention demonstrates (see, for example FIG. 9) that ODA ligands are bound tightly on the surface of the CdSe/CdS core/shell nanocrystals described herein. However, this is not the case for either the corresponding CdSe core nanocrystals (Qu, L.; Peng, X. *J. Am. Chem. Soc.* 2002, 124, 2049-2055, which is incorporated herein by reference in its entirety.) or the CdSe/CdS core/shell nanocrystals synthesized at relatively low temperatures (Peng, X.; Schlamp, M. C.; Kadavanich, A. V.; Alivisatos, A. P. *J. Am. Chem. Soc.* 1997, 119, 7019-7029, which is incorporated herein by reference in its entirety.). While not intending to be bound by this theory, the enhanced bonding between ODA and the CdSe/CdS core/shell nanocrystals described herein in comparison to the CdSe core nanocrystals can be explained by the relatively strong bonding of the CdS surface with electron donating species. The difference between the CdSe/CdS core/shell nanocrystals synthesized at different temperatures implies that higher temperatures promote the surface passivation with ODA, either through strong bonding of the ODA ligands, high surface coverage, or both.

Quantum Shells, Quantum Wells, Doped Nanocrystals, 0D-2D Nanocrystals, and Other Complex Structured Nanocrystals In another aspect, the present invention provides new types of colloidal materials including, but not limited to, quantum shells, quantum wells, doped nanocrystals, 0D-2D nanocrystals, and other complex structured nanocrystals.

As compared to core/shell nanocrystals with a small bandgap core and a large bandgap shell, with a type-I band offset, as described above, when the bandgap structure is reversed and a large bandgap is present for the core and a small bandgap is present for the shell material, the resulting core/shell semiconductor nanocrystals may approach the behavior of a two-dimensional (2D) system, for which the photo-generated holes and electrons are quantum confined inside the shell material only. While not intending to be bound by theory, for a 2D system, the diameter of the exciton is generally smaller than the perimeter of the shell in order to have the quantum confinement occur radially only. In this application, an "exciton" refers to the weakly bound electron-hole pair generated by photo-excitation. (See, for example: A. R. Kortan, R. Hull, R. L. Opila, M. G. Bawendi, M. L. Steigerwald, P. J. Carroll, L. E. Brus, *J. Am. Chem. Soc.* 112 (1990) 1327; A. Mews, A. Eychmueller, M. Giersig, D. Schooss, H. Weller, *J. Phys. Chem.* 98 (1994) 934; Y. Tian, T. Newton, N. A. Kotov, D. M. Guldi, J. H. Fendler, *J. Phys. Chem.* 100 (1996) 8927; R. B. Little, M. A. El-Sayed, G. W. Bryant, S. Burke, *J. Chem. Phys.* 114 (2001) 1813; each of which is incorporated by reference herein, in its entirety.)

Thus, in one aspect of this invention, quantum shells represent a new class of colloidal quantum structures grown by SILAR. In this aspect, for example, one difference between quantum shells and regular core/shells is the energy band gap offset between the core and shell materials. Thus, for quantum shells, the band gap of the shell is substantially smaller than that of the core material. As a result, the photo-generated excitons will be localized in the shell for quantum shells. While not intending to be bound by theory, if the diameter of the exciton of the shell material is smaller than the perimeter of the shell, the radial quantum confinement is so much stronger than the other two dimensions, this system behaves like a 2D system.

The number of possible quantum shell systems is very large. In one aspect of the invention, two specific examples of quantum shells, CdS/CdSe and CdS/InP, are described in detail herein. However, the present invention provides any colloidal core/shell semiconductor nanocrystal system with a narrow bandgap material as the shell and a wide bandgap material, including an insulator, as the core. Thus, the present invention comprises new compositions comprising quantum shells, new methods to prepare quantum shells, and new devices comprising quantum shells.

Traditional core/shell nanocrystals typically comprise a small bandgap core and a large bandgap shell. While not intending to be bound by theory, when the bandgap structure is reversed, a large bandgap for the core and a small bandgap for the shell material, the resulting core/shell semiconductor nanocrystals may behave like a two-dimensional (2D) system, for which the photo-generated holes and electrons are quantum confined inside the shell material only. Again, while not intending to be bound by theory, if the diameter of the photo-generated excitons is smaller than the perimeter of the shell, the quantum confinement only occurs radially. Thus, the present invention comprises these "reversed" bandgap structures comprising a large bandgap core and a small bandgap shell material, that results in quantum shells core/shell semiconductor nanocrystals.

Figure 12:
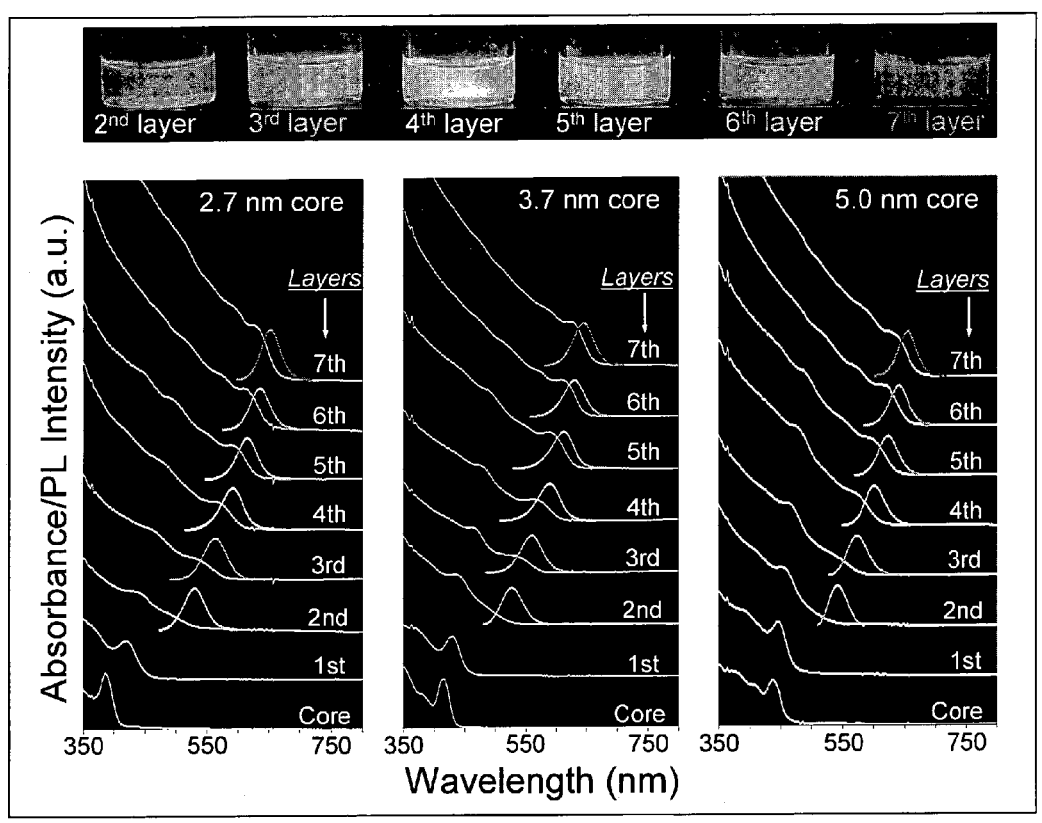
FIG. 12 provides a plot of the UV-Vis spectra of a series of CdS/CdSe quantum shells, which were examined after each sequential layer of CdSe was grown onto the plain CdS core, using SILAR methods.
Figure 13:
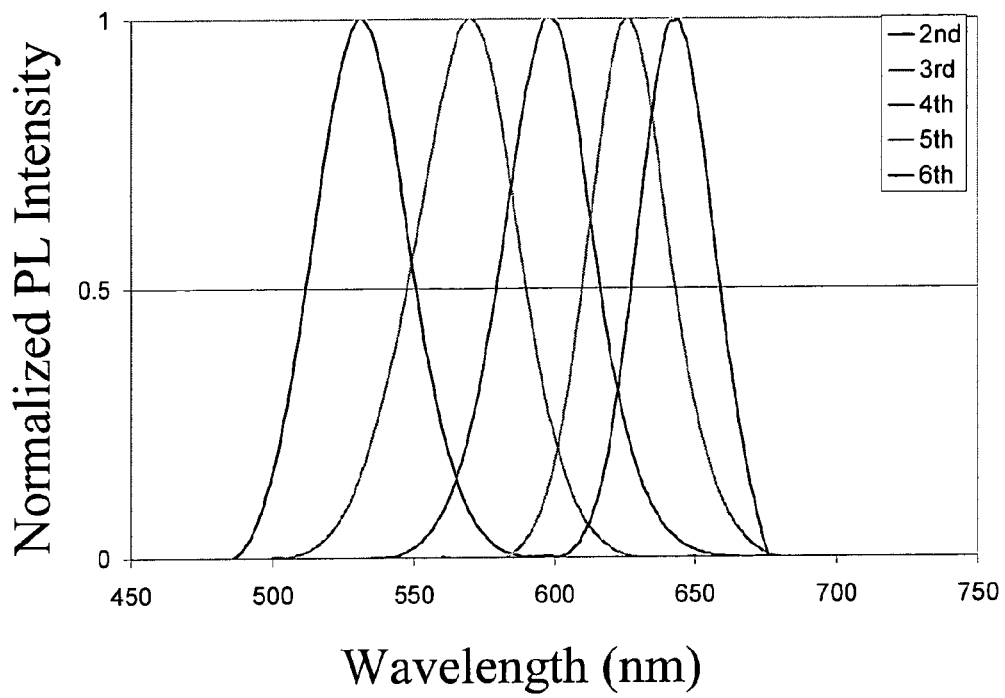
FIG. 13 presents an illustration of the PL Spectra of CdS/CdSe quantum shells which were examined after each sequential layer of CdSe was grown onto the plain CdS core, using SILAR methods, illustrating, among other things, the shift in wavelength.
Figure 14:
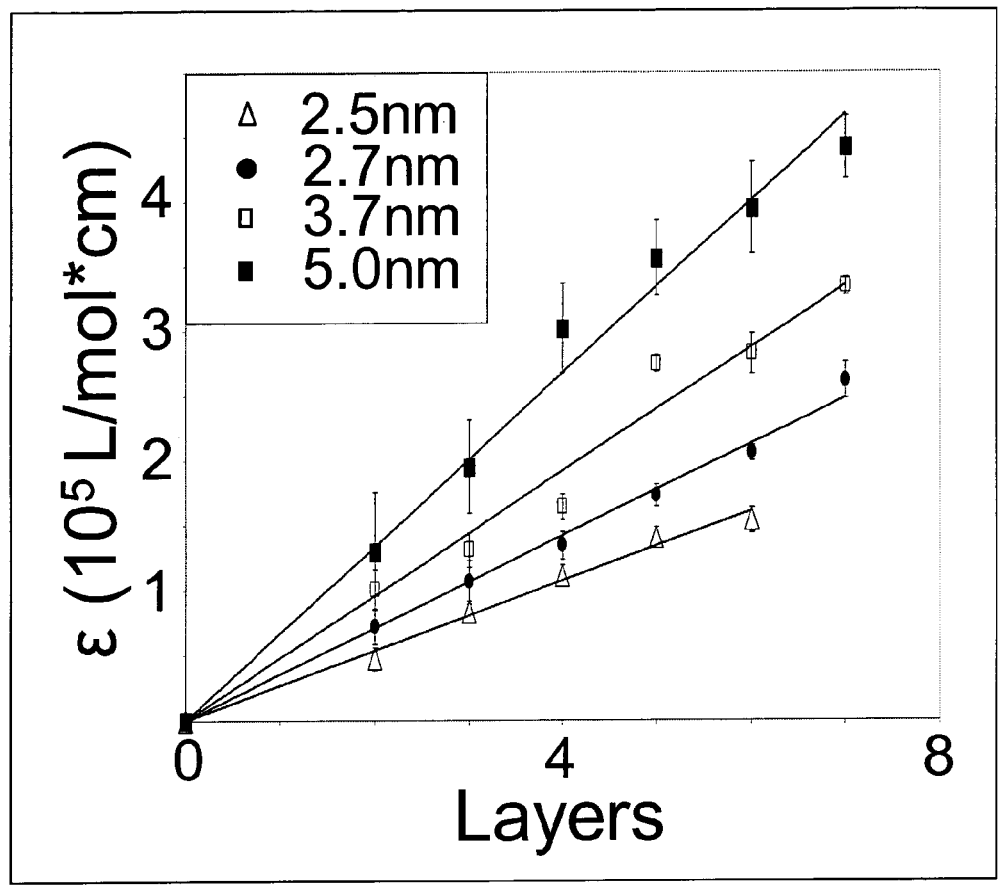
FIG. 14 provides an illustration of the layer-dependent molar extinction coefficient at the first absorption state for CdS/CdSe quantum shells. Quantum shells are shown to possess significantly lower molar extinction coefficients in comparison to the corresponding quantum dots. This feature, coupled with the large ensemble Stocks shift dramatically lowers the re-absorption of their photo- and electro-luminescence. Accordingly, the quantum shell nanocrystals are excellent emitters, especially when a high density of nanocrystals are needed for applications such as lasers and LEDs.

The unique optical properties of quantum shells make them excellent emitters for many applications. The global Stocks shifts of quantum shells (as illustrated in FIGS. 12 and 13) are significantly larger than the corresponding quantum dots, especially compared to medium and large sized quantum dots in the case of CdSe. The molar extinction coefficient at the emission peak wavelength of quantum shells, as illustrated in FIG. 14, is very small in comparison to the quantum dots with the same emission peak position. Therefore, it was discovered that quantum shells are expected to be ideal emitters when the re-absorption of photoluminescence or electroluminescence hinders the performance of a particular device. For example, performance may be affected by re-absorption and Foster energy transfer of photoluminescence or electroluminescence in solid state lasers, LEDs, in bio-medical labeling devices using semiconductor nanocrystals, especially if multiple labeling is employed.

Figure 15:
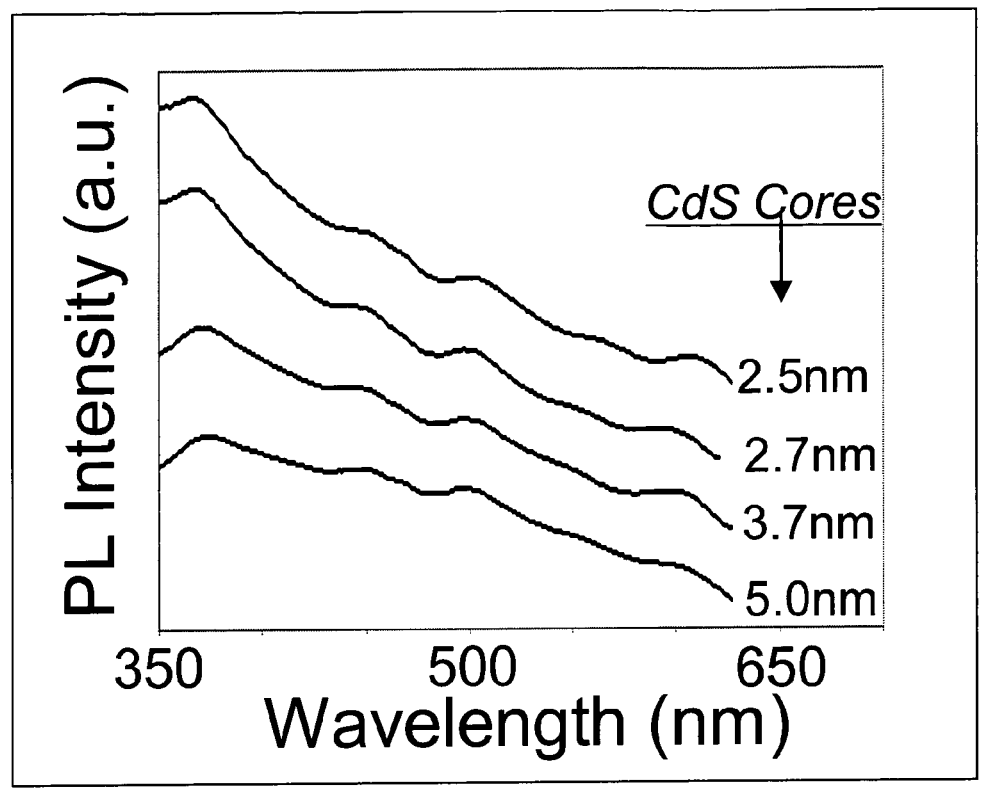
FIG. 15 illustrates the PLE (photoluminescence excitation) spectra of two samples of CdS/CdSe quantum shells with the same shell thickness (five monolayers) but different size cores, illustrating the similarity of the electronic energy states of these four systems, and suggesting a 1D confinement feature.

FIG. 15 provides the PLE spectra of two samples of CdS/CdSe quantum shells with a shell thickness of five monolayers applied to different size cores. The similarity of the electronic energy states of these two systems suggests a 1D confinement system.

Figure 17:
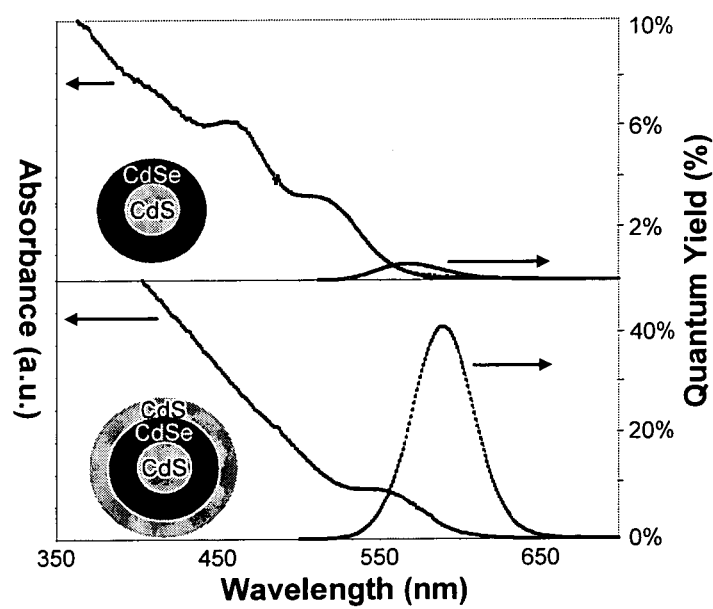
FIG. 17 illustrates the optical properties of CdS/CdSe/CdS quantum wells. For comparison, optical properties of the corresponding CdS/CdSe quantum shells are also illustrated at the top of this Figure.

In another aspect, more complex structured nanocrystals can also be grown using SILAR technique. For example, the growth of several monolayers of CdS onto the CdS/CdSe quantum shells was found to form a new class of nanocrystals, colloidal quantum wells. The resulting nanocrystals structurally and electronically resemble the Molecular-Beam-Epitaxy (MBE) quantum wells. The emission properties of quantum shells could be improved through inorganic passivation by additional epitaxial growth of a high bandgap semiconductor on the surface of the quantum shells in a one-pot approach. FIG. 17 shows the optical spectra before and after the epitaxial growth of four monolayers of CdS onto a CdSe quantum shell sample. As expected, the PL QY increased significantly after the inorganic overcoating and the PL peak position shifted to red. For inorganically-passivating quantum shells with CdS, it was seen that using fatty acids, including but not limited to oleic acid (OA) as ligands, yielded nanocrystals with higher quantum yields than did ones using amines. When fatty acids were used as the ligands, the CdSe quantum shells before the inorganic passivation did not emit well but did grow the desired monolayers on the CdS templates. This observation is consistent with the observation that fatty acids are better passivation ligands for CdS surfaces and amines are better choices for CdSe surface as discussed above.

In another aspect of this invention, and different from quantum shells, the present invention provides quantum wells, including, but not limited to, CdS/CdSe/CdS quantum wells. It was observed that those quantum wells with a single monolayer of CdSe emit very well. This observation is likely because of the inorganic passivation provided by the outer CdS shell. Typically, the PL QY increased for the quantum wells as the thickness of the outer CdS shell increased. The PL QY reached a plateau after about five to six monolayers of outer (second) shell CdS was deposited onto the quantum shells. The growth of quantum wells was performed in a single-pot fashion, which means that the quantum shells were not isolated before the deposition of the outer shell material onto the core/shell nanocrystal.

Figure 18:
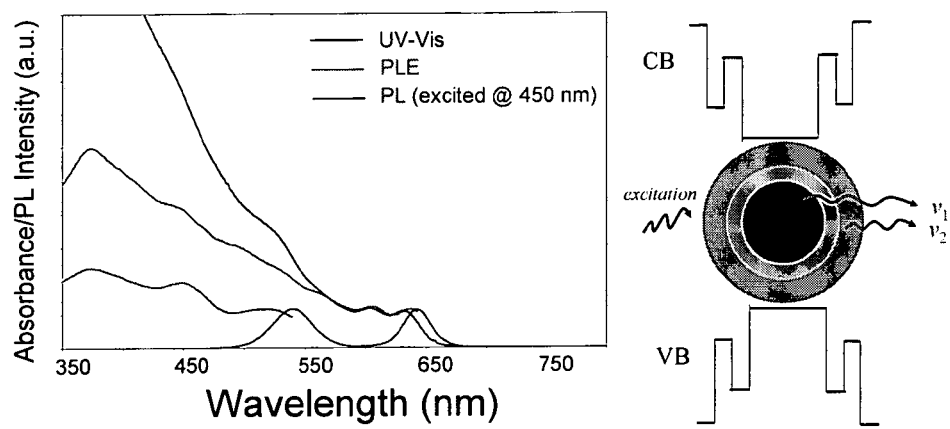
FIG. 18 illustrates the optical properties of dual-emitting CdSe/ZnS/CdSe nanocrystals, a type of 0D-2D hybrid nanocrystals. Refer to the schematic energy band structure shown on the right. The photoluminescence excitation (PLE) spectra shown here reveal that the emission at the low energy resembles that of zero-dimension (0D) nanocrystals, which is consistent with the core emission. Similarly, the PLE of the emission peak at the energy side resembles that of quantum shells (FIG. 15), indicating it is indeed from the quantum shell.

In another aspect of this invention, the SILAR technique was used for the formation of very complex structured nanocrystals. In one aspect, for example, CdSe/ZnS/CdSe nanocrystals represent one class of such complex nanocrystals. In this aspect, for example, the CdSe core behaves as 0D quantum system, and the CdSe outer shell constitutes a typical quantum shell similar to the ones described herein. The ZnS first shell acts as the energy barrier for the core and the quantum shell. Consequently, the core (0D) and the quantum shell (2D) cannot communicate electronically and will respond to photo-excitation or electronic-excitation independently. In this aspect, when the photoluminescence of the core is not or cannot be absorbed by the quantum shell, photoluminescence from both core and quantum shell can be observed, as illustrated in FIG. 18.

In another aspect of this invention, doped nanocrystals with a precise positioning of the dopants along the radial direction can be synthesized by the SILAR method. Such nanocrystals can be referred to as "radially-doped" or simply "doped" nanocrystals. For example, during the growth of a given monolayer, doping can be achieved by adding the dopants, either cationic or anionic, into the corresponding shell precursor solution.

In another aspect, this invention provides a composition comprising core/multiple shell nanocrystals which are optionally doped at the core and optionally doped at any shell. In this aspect, the present invention provides a composition comprising radially-doped, core/multiple shell nanocrystals, comprising:

1) a core material having the formula $M^1_{a-c}M^2_cE^1_b$, wherein:
   a) $M^1$ is selected from a metal, $E^1$ is selected from a non-metal, and a and b are dictated by the stoichiometry of the compound $M^1_aE^1_b$;
   b) $M^2$ is selected from a transition metal, a rare earth metal, or a mixture thereof; and $M^2$ is different than $M^1$; and
   c) $0 \leq c < a$;

2) an optional first shell material overcoating the core material, having the formula $M^3_{d-f}M^4_fE^3_e$, wherein:
   a) $M^3$ is selected from a metal, $E^3$ is selected from a non-metal, and d and e are dictated by the stoichiometry of the compound $M^3_dE^3_e$;
   b) $M^4$ is selected from a transition metal, a rare earth metal, or a mixture thereof; and $M^4$ is different than $M^3$; and
   c) $0 \leq f < d$;

3) an optional second shell material overcoating the optional first shell material, having the formula $M^5_{g-i}M^6_iE^5_h$, wherein:
   a) $M^5$ is selected from a metal, $E^5$ is selected from a non-metal, and g and h are dictated by the stoichiometry of the compound $M^5_gE^5_h$;
   b) $M^6$ is selected from a transition metal, a rare earth metal, or a mixture thereof; and $M^6$ is different than $M^5$; and
   c) $0 \leq i < g$;

4) an optional third shell material overcoating the optional second shell material, having the formula $M^7_{j-l}M^8_lE^7_k$, wherein:
   a) $M^7$ is selected from a metal, $E^7$ is selected from a non-metal, and j and k are dictated by the stoichiometry of the compound $M^7_jE^7_k$;
   b) $M^8$ is selected from a transition metal, a rare earth metal, or a mixture thereof; and $M^8$ is different than $M^7$; and
   c) $0 \leq l < j$; and 5) an optional fourth shell material overcoating the optional third shell material, having the formula $M^9_{m-o}M^{10}_oE^9_n$, wherein:
   a) $M^9$ is selected from a metal, $E^9$ is selected from a non-metal, and m and n are dictated by the stoichiometry of the compound $M^9_mE^9_n$;
   b) $M^{10}$ is selected from a transition metal, a rare earth metal, or a mixture thereof; and $M^{10}$ is different than $M^9$; and
   c) $0 \leq o < m$.

In another aspect, this invention provides a composition comprising radially-doped, core/multiple shell nanocrystals, wherein $M^1_aE^1_b$, $M^3_dE^3_e$, $M^5_gE^5_h$, $M^7_jE^7_k$, and $M^9_mE^9_n$ are independently selected from a compound or a III/V compound.

In yet another aspect, this invention provides a composition comprising radially-doped, core/multiple shell nanocrystals, wherein the thickness of the first shell material, the second shell material, the third shell, and the fourth shell material are independently varied between 1 and about 15 monolayers.

In another aspect, doped, core/multiple shell nanocrystals are characterized by a band gap of any shell material is less than the band gap of the both adjacent core or shell materials, or greater than the band gap of the both adjacent core or shell materials.

Still another aspect of this invention are core/multiple shell nanocrystals having the formula $M^1_{a-c}M^2_cE^1_b/M^3_{d-f}M^4_fE^3_e/M^5_{g-i}M^6_iE^5_h/M^7_{j-l}M^8_lE^7_k/M^9_{m-o}M^{10}_oE^9_n$, wherein:

a) i) $M^1$, $M^3$, $M^5$, $M^7$, and $M^9$ are independently selected from Zn, Cd, or Hg, and $E^1$, $E^3$, $E^5$, $E^7$, and $E^9$ are independently selected from O, S, Se, or Te; or ii) $M^1$, $M^3$, $M^5$, $M^7$, and $M^9$ are independently selected from Ga and In, and $E^1$, $E^3$, $E^5$, $E^7$, and $E^9$ are independently selected from N, P and As; and b) $M^2$, $M^4$, $M^6$, $M^8$, and $M^{10}$ are independently selected from Mn, Fe, Co, Ni, Pd, Pt, Cu, Al, Ag, or Au, or a rare earth metal. In another aspect, the doped core/multiple shell nanocrystals of this invention have the formula $M^1_{a-c}M^2_cE^1_b/M^3_{d-f}M^4_fE^3_e/M^5_{g-i}M^6_iE^5_h/M^7_{j-l}M^8_lE^7_k$; in another aspect, have the formula $M^1_{a-c}M^2_cE^1_b/M^3_{d-f}M^4_fE^3_e/M^5_{g-i}M^6_iE^5_h$; in yet another aspect, have the formula $M^1_{a-c}M^2_cE^1_b/M^3_{d-f}M^4_fE^3_e$; and in still another aspect, have the formula $M^1_{a-c}M^2_cE^1_b$.

In yet another aspect, the present invention provides doped core/multiple shell nanocrystal having the formula $M^1_{a-c}M^2_cE^1_b/M^3_{d-f}M^4_fE^3_e/M^5_{g-i}M^6_iE^5_h/M^7_{j-l}M^8_lE^7_k/M^9_{m-o}M^{10}_oE^9_n$, wherein $M^3_{d-f}M^4_fE^3_e$, $M^5_{g-i}M^6_iE^5_h$, $M^7_{j-l}M^8_lE^7_k$, and $M^9_{m-o}M^{10}_oE^9_n$ constitute optional shell layers that are optionally doped, and wherein $M^1_aE^1_b$, $M^3_dE^3_e$, $M^5_gE^5_h$, $M^7_jE^7_k$, and $M^9_mE^9_n$ are independently selected from CdSe, CdS, CdTe, ZnS, ZnSe, ZnTe, HgS, HgSe, HgTe, InAs, InP, GaAs, GaP, ZnO, CdO, HgO, $In_2O_3$, $TiO_2$, or a rare earth oxide.

In another aspect, the present invention provides doped core/multiple shell nanocrystals, wherein:

a) the nanocrystals comprise a core material, a first shell material, and a second material; and have the formula $M^1_{a-c}M^2_cE^1_b/M^3_{d-f}M^4_fE^3_e/M^5_{g-i}M^6_iE^5_h$; and b) the nanocrystals comprise $ZnSe/Zn_{d-f}M^4_fSe/ZnSe$, $ZnSe/Zn_{d-f}M^4_fSe/ZnS$, $ZnO/Zn_{d-f}M^4_fO/ZnO$, $ZnO/Zn_{d-f}M^4_fO/ZnS$, $TiO_2/Ti_{d-f}M^4_fO_2/TiO_2$, and wherein $M^4$ is selected from Mn, Fe, Co, Ni, Pd, Pt, Cu, Al, Ag, or Au, or a rare earth metal.

In still another aspect, this invention provides a method for preparing radially-doped core/multiple shell nanocrystals comprising a doped core material having the formula $M^1_{a-c}M^2_cE^1_b$, an optional doped first shell material having the formula $M^3_{d-f}M^4_fE^3_e$ and overcoating the core material, an optional doped second shell material having the formula $M^5_{g-i}M^6_iE^5_h$ and overcoating the first core material, an optional doped third shell material having the formula $M^7_{j-l}M^8_lE^7_k$ and overcoating the second core material, and an optional doped fourth shell material having the formula $M^9_{m-o}M^{10}_oE^9_n$ and overcoating the third core material, comprising:

a) providing a solution of core nanocrystals of the formula $M^1_aE^1_b$, wherein $M^1$ is selected from a metal, $E^1$ is selected from a non-metal, and a and b are dictated by the stoichiometry of the compound;

b) optionally forming at least one monolayer of a doped core material of the formula $M^1_{a-c}M^2_cE^1_b$ by contacting the nanocrystals, in an alternating manner, with a first cation precursor solution in an amount effective to form a monolayer of a first cation $M^1$, optionally doped with a second cation $M^2$, and a first anion ($E^1$) precursor solution in an amount effective to form a monolayer of the first anion;

wherein the first cation precursor solution comprises a first cation ($M^1$) precursor and an optional second cation ($M^2$) precursor; and wherein $M^2$ is selected from a transition metal, a rare earth metal, or a mixture thereof; $M^2$ is different than $M^1$; and $0 \leq c < a$;

c) optionally forming at least one monolayer of a doped first shell material of the formula $M^3_{d-f}M^4_fE^3_e$ by contacting the nanocrystals, in an alternating manner, with a second cation precursor solution in an amount effective to form a monolayer of a third cation $M^3$, optionally doped with a fourth cation $M^4$, and a second anion ($E^3$) precursor solution in an amount effective to form a monolayer of the second anion;

wherein the second cation precursor solution comprises a third cation ($M^3$) precursor and an optional fourth cation ($M^4$) precursor; and wherein $M^3$ is selected from a metal, $E^3$ is selected from a non-metal, and d and e are dictated by the stoichiometry of the compound $M^3_dE^3_e$;

wherein $M^4$ is independently selected from a transition metal, a rare earth metal, or a mixture thereof; $M^4$ is different than $M^3$; and $0 \leq f < d$;

d) optionally repeating step c to form optional doped shells $M^5_{g-i}M^6_iE^5_h$, $M^7_{j-l}M^8_lE^7_k$, and $M^9_{m-o}M^{10}_oE^9_n$, wherein $M^5$, $M^7$, and $M^9$ are independently selected from a metal; $M^6$, $M^8$, and $M^{10}$ are independently selected from a transition metal, a rare earth metal, or a mixture thereof; $E^5$, $E^7$, and $E^9$ are independently selected from a non-metal; g and h are dictated by the stoichiometry of the compound $M^5_gE^5_h$; j and k are dictated by the stoichiometry of the compound $M^7_jE^7_k$, m and n are dictated by the stoichiometry of the compound $M^9_mE^9_n$; $0 \leq i < g$; $0 \leq l < j$; and $0 \leq o < m$.

In this aspect, for example, this method can be used for preparing doped core/multiple shell nanocrystals wherein:

a) i) $M^1$, $M^3$, $M^5$, $M^7$, and $M^9$ are independently selected from Zn, Cd, or Hg, and $E^1$, $E^3$, $E^5$, $E^7$, and $E^9$ are independently selected from O, S, Se, or Te; or ii) $M^1$, $M^3$, $M^5$, $M^7$, and $M^9$ are independently selected from Ga and In, and $E^1$, $E^3$, $E^5$, $E^7$, and $E^9$ are independently selected from N, P and As; and b) $M^2$, $M^4$, $M^6$, $M^8$, and $M^{10}$ are independently selected from Mn, Fe, Co, Ni, Pd, Pt, Cu, Al, Ag, or Au, or a rare earth metal.

In another aspect, for example, this method can be used for preparing doped core/multiple shell nanocrystals wherein $M^1_aE^1_b$, $M^3_dE^3_e$, $M^5_gE^5_h$, $M^7_jE^7_k$, and $M^9_mE^9_n$ are independently selected from CdSe, CdS, CdTe, ZnS, ZnSe, ZnTe, HgS, HgSe, HgTe, InAs, InP, GaAs, GaP, ZnO, CdO, HgO, $In_2O_3$, $TiO_2$, or a rare earth oxide.

In another aspect, for example, this method can be used for preparing doped core/multiple shell nanocrystals wherein $M^1_aE^1_b$, $M^3_dE^3_e$, $M^5_gE^5_h$, $M^7_jE^7_k$, and $M^9_mE^9_n$ are independently selected from a II/VI compound or a III/V compound.

In still another aspect, the thickness of the first shell material, the second shell material, the third shell, and the fourth shell material are independently varied between 1 and about 15 monolayers.

In yet another aspect, the band gap of any shell material is less than the band gap of the both adjacent core or shell materials, or greater than the band gap of the both adjacent core or shell materials.

In another aspect, for example, this method can be used for preparing doped core/multiple shell nanocrystals wherein:

a) i) $M^1$, $M^3$, $M^5$, $M^7$, and $M^9$ are independently selected from Zn, Cd, or Hg, and $E^1$, $E^3$, $E^5$, $E^7$, and $E^9$ are independently selected from O, S, Se, or Te; or ii) $M^1$, $M^3$, $M^5$, $M^7$, and $M^9$ are independently selected from Ga and In, and $E^1$, $E^3$, $E^5$, $E^7$, and $E^9$ are independently selected from N, P and As; and b) $M^2$, $M^4$, $M^6$, $M^8$, and $M^{10}$ are independently selected from Mn, Fe, Co, Ni, Pd, Pt, Cu, Al, Ag, or Au, or a rare earth metal.

In yet another aspect, for example, this method can be used for preparing doped core/multiple shell nanocrystals wherein $M^1{}_a E^1{}_b$, $M^3{}_d E^3{}_e$, $M^5{}_g E^5{}_h$, $M^7{}_j E^7{}_k$, and $M^9{}_m E^9{}_n$ are independently selected from CdSe, CdS, CdTe, ZnS, ZnSe, ZnTe, HgS, HgSe, HgTe, InAs, InP, GaAs, GaP, ZnO, CdO, HgO, In$_2$O$_3$, TiO$_2$, or a rare earth oxide.

In yet another aspect, for example, this method can be used for preparing doped core/multiple shell nanocrystals wherein a) the nanocrystals comprise a core material, a first shell material, and a second material; and have the formula $M^1{}_{a-c}M^2{}_c E^1{}_b/M^3{}_{d-f}M^4{}_f E^3{}_e/M^5{}_{g-i}M^6{}_i E^5{}_h$; and b) the nanocrystals comprise ZnSe/Zn$_{d-f}$M$^4{}_f$Se/ZnSe, ZnSe/Zn$_{d-f}$M$^4{}_f$Se/ZnS, ZnO/Zn$_{d-f}$M$^4{}_f$O/ZnO, ZnO/Zn$_{d-f}$M$^4{}_f$O/ZnS, TiO$_2$/Ti$_{d-f}$M$^4{}_f$O$_2$/TiO$_2$, and wherein $M^4$ is selected from Mn, Fe, Co, Ni, Pd, Pt, Cu, Al, Ag, or Au, or a rare earth metal.

While not intending to be bound by the following statement, it is believed that the methods disclosed herein are effective because the reactivity of the precursors are weak enough to prevent their independent nucleation, but sufficiently strong to promote the epitaxial growth around the existing core nanocrystals. Therefore, relatively stable and less reactive precursors are expected to be more suited for the growth of high quality core/shell nanocrystals than the traditional organometallic precursors, such as dimethyl cadmium, dimethyl zinc and trimethylsilane sulfide. (See: Qu, L.; Peng, Z. A.; Peng, X. *Nano Lett.* 2001, 1, 333, which is incorporated by reference herein, in its entirety.)

An additional advantage of this invention is that the relatively stable and less reactive precursors are also relatively inexpensive, more safe, and more environmentally benign, as compared to the traditional organometallic precursors. These methods also employ non-coordinating solvents which not only provide the necessary tunability of the reactivity of the monomers by varying the ligand concentration in solution, but are also more environmentally safe.

Thus, in one aspect, this invention provides a composition comprising nanocrystalline, core/shell quantum shells, wherein:

the quantum shells comprise a core material and a shell material overcoating the core material;

the core material comprises a stable, nanometer-sized inorganic solid;

the shell material overcoating the core material is selected from a II/VI compound or a III/V compound;

the band gap of the core material is greater than the band gap of the shell material;

the thickness of the shell material is from 1 to about 15 monolayers; and the as-prepared quantum shells having the shell thickness greater than 1 monolayer exhibit a photoluminescence that is substantially limited to a bandgap emission, with a photoluminescence quantum yield (PL QY) up to about 20%.

In another aspect, the core material can comprise a II/VI compound or a III/V compound. In yet another aspect, the nanocrystalline, core/shell quantum shells of this invention are characterized by photogenerated excitons that are substantially localized in the shell of the quantum shells. In still another aspect, the quantum shells can exhibit a type-I band offset. In a further aspect, the core of the quantum shells can comprise an insulator.

Still another aspect of this invention is a quantum shell that can comprise CdS/CdSe, CdS/InP, CdS/CdTe, ZnS/CdS, ZnS/CdSe, ZnS/ZnSe, ZnS/CdTe, ZnSe/CdSe, ZnSe/InP, CdS/InAs, CdSe/InAs, ZnSe/InAs, ZnS/InAs, InP/InAs, or a mixture thereof.

In another aspect, the quantum shells of this invention can photoluminesce at a wavelength from about 400 to about 1000 nm. In this aspect, the photogenerated excitons are typically radially quantum confined in the shell of the quantum shells. Further, in this aspect, the quantum shells can exhibit a photoluminescence emission line characterized by a FWHM of about 60 nm or less, about 55 nm or less, about 50 nm or less, about 45 nm or less, about 40 nm or less, about 35 nm or less, about 30 nm or less, about 28 nm or less, or about 25 nm or less.

In another aspect, the quantum shells of this invention are substantially monodisperse. In this aspect, the quantum shells can be characterized by a size distribution having a standard deviation no greater than about 15% of a mean diameter of the population of quantum shells, no greater than about 12% of a mean diameter of the population of quantum shells, no greater than about 10% of a mean diameter of the population of quantum shells, no greater than about 7% of a mean diameter of the population of quantum shells, or no greater than about 5% of a mean diameter of the population of quantum shells.

In another aspect, this invention provides devices comprising the quantum shells and compositions of this invention, including, but not limited to, light-emitting diodes, biological labeling agents, photoelectric devices, lasers, and the like.

In still another aspect, this invention provides a composition comprising nanocrystalline, core/shell/shell quantum wells, wherein:

the quantum wells comprise a core material, a first shell material overcoating the core material, and a second shell material overcoating the first shell material; the core material comprises a stable, nanometer-sized inorganic solid;

the first shell material and the second shell material are independently selected from a II/VI compound or a III/V compound;

the band gap of the first shell material is less than the band gap of the core material and less than the band gap of the second shell material; and the as-prepared quantum wells exhibit a photoluminescence that is substantially limited to a bandgap emission, with a photoluminescence quantum yield (PL QY) up to about 50%.

In this aspect, the core material can comprise a II/VI compound or a III/V compound. Further, the core material of the quantum wells can comprise an insulator.

In another aspect, for example, the quantum wells of this invention can comprise CdS/CdSe/CdS, CdS/CdSe/ZnSe, CdS/CdSe/ZnS, ZnSe/CdSe/CdS, ZnSe/CdSe/ZnSe, ZnSe/CdSe/ZnS, ZnS/CdSe/ZnS, ZnS/CdSe/CdS, ZnS/CdSe/ZnSe, ZnS/CdS/ZnS, ZnS/ZnSe/ZnS, CdS/InP/CdS, CdS/InP/ZnSe, CdS/InP/ZnS, ZnSe/InP/ZnSe, ZnSe/InP/CdS, ZnSe/InP/ZnS, ZnS/InP/ZnS, ZnS/InP/CdS, ZnS/InP/ZnSe, CdS/InAs/CdS, CdS/InAs/ZnSe, CdS/InAs/ZnS, ZnSe/InAs/ZnSe, ZnSe/InAs/CdS, ZnSe/InAs/ZnS, ZnS/InAs/ZnS, ZnS/InAs/CdS, ZnS/InAs/ZnSe, CdSe/InAs/CdSe, CdSe/InAs/CdS, CdSe/InAs/ZnS, CdSe/InAs/ZnSe, InAs/InP/CdS, or a mixture thereof. Thus, in another aspect, the core material and the second shell material are the same.

In another aspect, this invention provides devices comprising the quantum wells and compositions of this invention, including, but not limited to, light-emitting diodes, biological labeling agents, photoelectric devices, lasers, and the like.

In yet another aspect, this invention provides a composition comprising nanocrystalline, core/multiple shell quantum wells, wherein:

the quantum wells comprise a core material, a first shell material overcoating the core material, a second shell material overcoating the first shell material, and optionally comprising additional shell materials sequentially overcoating underlying shells;

the core material comprises a stable, nanometer-sized inorganic solid;

the first shell material and the second shell material are independently selected from a II/VI compound or a III/V compound;

any additional shells are selected from the first shell material and the second shell material such that the composition of the additional shells alternates between the first shell material and the second shell material; and the band gap of the first shell material is less than the band gap of the core material and less than the band gap of the second shell material.

In this aspect, the core material can comprise a II/VI compound or a III/V compound. Further in this aspect, the core material of the quantum wells can comprise an insulator. In yet another aspect, the as-prepared quantum wells can exhibit a photoluminescence that is substantially limited to a bandgap emission, with a photoluminescence quantum yield (PL QY) up to about 10%, up to about 20%, up to about 30%, up to about 40%, up to about 50%, or up to about 60%.

In another aspect, this invention provides a composition comprising radially-doped (or, simply "doped"), core/shell/shell nanocrystals wherein:

the radially-doped nanocrystals comprise a core material, a first shell material overcoating the core material, and a second shell material overcoating the first shell material;

the core material comprises a compound of the formula $M^1_xE_y$, wherein $M^1$ is selected from a metal, E is selected from a non-metal, and x and y are dictated by the stoichiometry of the compound;

the first shell material comprises a compound of the formula $M^1_{x-z}M^2_zE_y$, wherein $M^2$ is selected from a transition metal or a mixture thereof, $0 \leq z < x$, and $M^2$ is different than $M^1$; and the second shell material comprises a compound of the formula $M^1_{x-q}M^3_qE_y$, wherein $M^3$ is selected from a transition metal, a rare earth metal, or a mixture thereof, $0 \leq q \leq x$, and x is not equal to q when $M^2$ is the same as $M^3$.

In another aspect, the doped nanocrystals of this invention can be characterized by:

a) i) $M^1$ is selected from Zn, Cd, or Hg, and E is selected from O, S. Se, or Te; or
    ii) $M^1$ is selected from Ga and In, and E is selected from N, P and As; and b) $M^2$ is selected from Mn, Fe, Co, Ni, Pd, Pt, Cu, Al, Ag, or Au, or a rare earth metal.

In another aspect of the doped nanocrystals of this invention, $M^1_xE_y$ can be selected from CdSe, CdS, CdTe, ZnS, ZnSe, ZnTe, HgS, HgSe, HgTe, InAs, InP, GaAs, GaP, ZnO, CdO, HgO, $In_2O_3$, $TiO_2$, or a rare earth oxide. In another aspect of the doped nanocrystals of this invention, the radially-doped, core/shell/shell nanocrystals comprise $ZnSe/Zn_{x-z}M^2_zSe/ZnSe$, $ZnSe/Zn_{x-z}M^2_zSe/ZnS$, $ZnO/Zn_{x-z}M^2_zO/ZnO$, $ZnO/Zn_{x-z}M^2_zO/ZnS$, $TiO_2/Ti_{x-z}M^2_zO_2/TiO_2$, and wherein $M^2$ is selected from Mn, Fe, Co, Ni, Pd, Pt, Cu, Al, Ag, or Au, or a rare earth metal.

In a further aspect, this invention provides a composition comprising core/shell/shell dual-emitting nanocrystals, wherein:

the nanocrystals comprise a core material, a first shell material overcoating the core material, and a second shell material overcoating the first shell material, each of which is independently selected from a II/VI compound or a III/V compound;

the band gap of the first shell material is greater than the band gap of the core material and greater than the band gap of the second shell material; and the as-prepared dual-emitting nanocrystals exhibit a photoluminescence comprising bandgap emission peaks.

In one aspect, the dual-emitting nanocrystals can further comprise at least one additional shell material sequentially overcoating underlying shells, wherein:

the additional shell materials are independently selected from a II/VI compound or a III/V compound; and the band gap of the additional shell materials are greater than the band gap of the second shell material.

In this aspect, the dual-emitting nanocrystals can further comprise up to about 15 additional shells, comprising shell materials wherein:

the additional shell materials are independently selected from selected from a II/VI compound or a III/V compound; and the band gap of the additional shell materials are greater than the band gap of the second shell material.

In a further aspect, the present invention provides a composition comprising core/shell/shell/shell dual-emitting nanocrystals, wherein:

the nanocrystals comprise a core material, a first shell material overcoating the core material, a second shell material overcoating the first shell material, and a third shell material overcoating the second shell material, each of which is independently selected from a II/VI compound or a III/V compound;

the band gap of the first shell material and the band gap of the third shell material are less than the band gap of the core material and are less than the band gap of the second shell material; and the as-prepared dual-emitting nanocrystals exhibit a photoluminescence comprising two bandgap emissions.

In yet another invention, this invention provides a composition comprising core/multiple shell nanocrystals, wherein:

the nanocrystals comprise a core material, a first shell material overcoating the core material, a second shell material overcoating the first shell material, a third shell material overcoating the second shell material, a fourth shell material overcoating the third shell material, and optionally additional shells overcoating underlying shells, each of which is independently selected from a II/VI compound or a III/V compound;

the band gap of any shell material is less than the band gap of the both adjacent core or shell materials, or greater than the band gap of the both adjacent core or shell materials.

In another aspect of this invention, the present invention provides a method for preparing radially-doped core/shell/shell nanocrystals having the formula $M^1_xE_y/M^1_{x-z}M^2_zE_y/M^1_{x-q}M^3_qE_y$, comprising:

a) providing a solution of core nanocrystals of the formula $M^1_xE_y$, wherein $M^1$ is selected from a metal, E is selected from a non-metal, and x and y are dictated by the stoichiometry of the compound;

b) forming at least one monolayer of a doped first shell material of the formula $M^1_{x-z}M^2_zE_y$ by contacting the core nanocrystals, in an alternating manner, with a cation precursor solution in an amount effective to form a monolayer of the first cation doped with the second cation, and a first anion ($X^2$) precursor solution in an amount effective to form a monolayer of the first anion;

wherein the cation precursor solution comprises a first cation ($M^1$) precursor, a second cation ($M^2$) precursor, or a combination thereof, and wherein $M^2$ is selected from a transition metal or a mixture thereof, $0 \leq z < x$, and $M^2$ is different than $M^1$;

c) forming at least one monolayer of a second shell material of the formula $M^1_{x-q}M^3_qE_y$ by contacting the core/shell nanocrystals, in an alternating manner, with a first cation precursor solution in an amount effective to form a monolayer of the first cation, and an second anion ($X^3$) precursor solution in an amount effective to form a monolayer of the first anion;

wherein the first cation precursor solution optionally comprises a third cation ($M^3$) precursor selected from a transition metal, a rare earth metal, or a mixture thereof; and wherein $0 \leq q \leq x$, and x is not equal to q when $M^2$ is the same as $M^3$; and d) optionally repeating steps b and c to form additional shells overcoating the second shell.

In another aspect of this method, $M^1E$ can be selected from a II/VI compound or a compound. In yet another aspect, q is 0, therefore in this aspect, the core material and the second shell material have the formula $M^1_xE_y$.

Definitions

In order to more clearly define the terms used herein, the following definitions are provided. To the extent that any definition or usage provided by any document incorporated herein by reference conflicts with the definition or usage provided herein, the definition or usage provided herein controls.

As used herein, the term II/VI compound or II/VI material refers to a compound comprising a group II element (also referred to as a group 12 element) and a group VI element (also referred to as group 16 element). In this aspect, the group II elements are Zn, Cd, or Hg; and the group VI elements are O, S, Se, or Te.

Similarly, as used herein, the term III/V compound or III/V material refers to a compound comprising a group III element (also referred to as a group 13 element) and a group V element (also referred to as group 15 element). In this aspect, the group III elements are B, Al, Ga, In, or Tl; and the group VI elements are N, P, As, Sb, and Bi.

As used herein transition metals include, but not limited to, Ti, Zr, Hf, V, Nb, Ta, Cr, Mo, W, Mn, Tc, Re, Fe, Ru, Os, Co, Rh, Ir, Ni, Pd, Pt, Cu, Ag, and Au. (See, F. A. Cotton et al., Advanced Inorganic Chemistry, 6th Edition, (1999).) As used herein, including in the context of providing core materials, Sc, Y, and La are also considered transition metals.

As used herein, the term "stable" refers to both thermal and chemical stability, in the context of stability under the reactions conditions used to prepared the nanocrystals of the present invention. Thus, stability to oxidation; reduction; reaction with acids; reaction with bases; electron transfer reactions; internal bond-making; bond-breaking; rearrangement reactions; or any other type of internal reactions or reactions with external reagents are included in this definition. In this aspect, for example, the nanometer-sized inorganic core materials may be referred to as comprising a stable, nanometer-sized inorganic solid which refers to their being thermally and chemically stable under the reaction conditions used to prepare nanocrystals of the present invention.

The term "as-prepared", as used herein, generally refers to samples of nanocrystals that are used without purification or size-selection methods. Specifically, "as-prepared" nanocrystals or nanocrystalline products refer to those nanocrystal samples dissolved in the original reaction mixture or diluted by a solvent without the removal of any unreacted reactants and the side products.

The term rare-earth or rare-earth metal, as used herein, refers to the lanthanides, the actinides, and Sc, Y, and La. Thus, in this aspect, Sc, Y, and La are encompassed by the terms transition metal and rare-earth metal.

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to one of ordinary skill in the art without departing from the spirit of the present invention or the scope of the appended claims.

In the following examples, cadmium oxide (CdO, 99.99%), selenium (Se, 99.5%, 100 mesh), sulfur (S, 99.98%, powder), trioctylphosphine oxide (TOPO, 90%), tributylphosphine (TBP, 97%), 1-octadecene (ODE), oleic acid (OA, 90%) and octadecylamine (ODA, 97%) were each purchased from Aldrich and were used without further purification. Stearic acid (99%) was obtained from Avocado and was used as received. All organic solvents were purchased from EM Sciences and were likewise used directly without any further purification.

Example 1

Synthesis of CdSe Core Nanocrystals

Highly fluorescent CdSe nanocrystals were prepared as described in the following typical reaction. A mixture of 0.2 mmol (25.6 mg) of CdO, 0.8 mmol (227 mg) of stearic acid, and 2 g of ODE was prepared in a 25 mL, three-necked flask, and this mixture was heated to about 200° C. to form a clear, colorless solution. The solution was then cooled to room temperature, and 1.5 g of ODA and 0.5 g of TOPO were subsequently added. Under an argon flow, this mixture was reheated to 280° C. A selenium stock solution, prepared by dissolving 2 mmol (158 mg) of Se in 0.472 g of TBP and diluting the solution with 1.37 g of ODE, was quickly injected at this injection temperature of 280° C. The mixture was then maintained at the growth temperature of 250° C. until the desired size of the nanocrystals was obtained.

Figure 16:
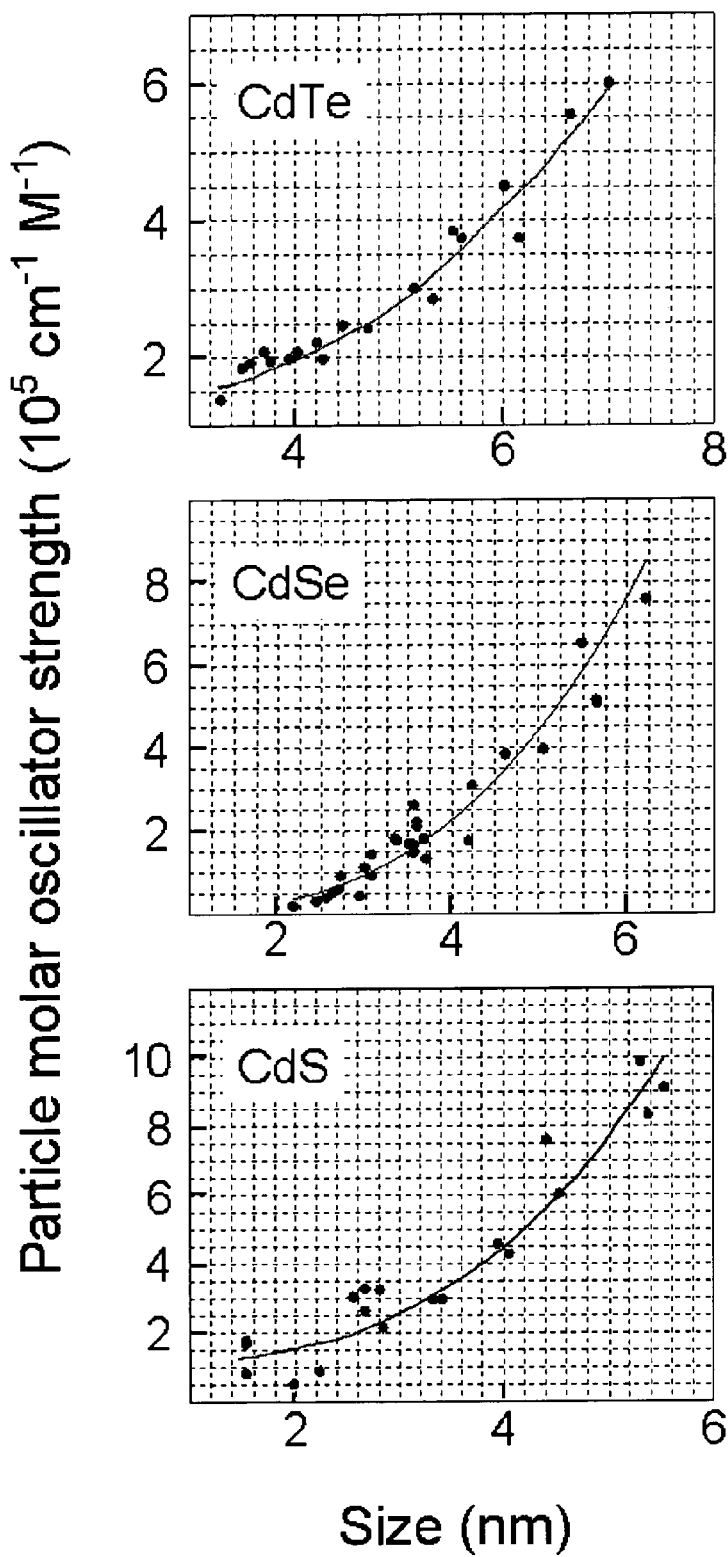
FIG. 16 presents extinction coefficients of various nanocrystals as a function of nanocrystal size.

This reaction generated CdSe nanocrystals of about 3.5 nm in size, characterized by having a first absorption peak around 570 nm. The reaction mixture was allowed to cool to room temperature, and the resulting nanocrystals were purified from side products and unreacted precursors using the following extraction procedure. A large volume of methanol (at least 3 times of the volume of the reaction mixture) and a small volume of hexanes (about equal volume of the reaction mixture) were mixed with the reaction mixture, and the unreacted precursors and excess amines were extracted into the methanol layer. The particle concentration of the purified CdSe solution in hexanes, as stock solution for core/shell growth, was measured by using Beer's law with the extinction coefficients of CdSe nanocrystals. Extinction coefficients of various nanocrystals as a function of nanocrystal size, including CdSe nanocrystals, are presented in FIG. 16. The TOPO-coated CdSe nanocrystals were synthesized using the procedure described in Aldana, J.; Wang, Y.; Peng, X. *J. Am. Chem. Soc.* 2001, 123, 8844, which is incorporated herein by reference in its entirety.

Example 2

Synthesis of Cadmium (Cation Precursor) and Sulfur (Anion Precursor) Injection Solutions Synthesis of the cadmium sulfide shell material for various core/shell nanocrystals, for example, the CdSe/CdS core/shell nanocrystals, was accomplished at relatively low temperatures by using the following injection solutions for the cation precursor cadmium and the anion precursor sulfur, respectively. The cadmium injection solution (0.04 M) was prepared by dissolving CdO (0.615 g) in oleic acid (OA, 10.83 g), and 1-octadecene (ODE, 108 mL), at 250° C. The sulfur injection solution (0.04 M) was prepared by dissolving sulfur in ODE at 200° C. Both injection solutions were prepared under an argon flow. After clear solutions were obtained, the cadmium injection solution was allowed to cool to about 60° C. for use, while the sulfur injection solution was allowed to cool to room temperature for use. For each injection, a calculated amount of a given injection solution was taken with a syringe using standard air-free procedures.

Example 3

Calculations for the Injection Procedure Using the Cadmium and Sulfur Injection Solutions The successive ionic layer adsorption and reaction (SILAR) technique employed herein, also termed the solution atomic layer epitaxy (SALE) technique, was based on the alternating injections of the cation injection solution and the anion injection solution, into a solution containing the core nanocrystals. For example, as applied to the growth of CdSe/CdS core/shell nanocrystals, the SILAR technique disclosed herein was based on the alternating injections of the Cd injection solution and the S injection solution, into a solution containing CdSe nanocrystals.

The amount of cadmium or sulfur, and hence the amount of injection solution, needed for each layer was determined by calculating the number of surface atoms of a given sized core/shell nanocrystal. Since there is only about a 5-6% lattice mismatch between CdSe and CdS bulk crystals, the calculations were based on the wurtzite structure of CdSe nanocrystals. On average, the thickness of one monolayer of CdS was assumed as 0.35 nm, so one additional layer growth would increase the size of the nanocrystals by about 0.7 nm in diameter. For example, in a typical experiment with $1 \times 10^{-5}$ mmol of 3.7 mm core CdSe particles, $2.13 \times 10^{-3}$ mmol of the Cd and S precursors are needed for the first layer of the shell growth, and additional $2.85 \times 10^{-3}$ mmol of the Cd and S precursors will complete the growth of the second layer.

Example 4

Synthesis of CdSe/CdS Core/Shell Nanocrystals Using the Successive Ionic Layer Adsorption and Reaction (SILAR) Technique In a typical successive ionic layer adsorption and reaction (SILAR) technique preparation of CdSe/CdS core/shell nanocrystals, alternating injections of the Cd and S injection solutions into a CdSe nanocrystal-containing solution were carried out. A stock solution of 2.44 g of CdSe nanocrystals in hexanes, 3.5 nm in diameter and $1.01 \times 10^{-4}$ mmol in hexanes, was mixed with 1.5 g of ODA and 5.0 g of ODE in a 25 mL, three-necked flask. The flask was then sealed and placed under vacuum at room temperature for 30 min to remove the hexanes, then heated to 100° C. while still under vacuum for another 5-10 min to remove any residual air from the system. After this procedure, the CdSe nanocrystal-containing solution was placed under an argon flow and the reaction mixture was further heated to 240° C. in preparation for injections. The first injection was made using 0.49 mL of the Cd injection solution (0.04 M). The amounts of the injection solutions were calculated for each subsequent injection using the method described above. To monitor the reaction, aliquots were taken at the first minute after injection and subsequently every 3-5 min, and absorption measurements of each aliquot were examined. If there was no observable change in the UV-Vis absorption spectrum for two successive aliquots 3-5 min separated, the injection of another shell component for either the same layer (nS) or the next layer ((n+1)Cd) was executed.

After no further UV-Vis peak shift was observed in 5 min following the fifth sulfur injection, the reaction was terminated by allowing the reaction mixture to cool to room temperature. The final product was purified by diluting the reaction solution with hexanes, and the contaminants were extracted from the hexane solution with methanol. Alternatively, the resulting nanocrystals were precipitated by adding acetone to the hexanes solution. Excess amines were further removed by dissolving the nanocrystals in chloroform and precipitating them with acetone.

The reaction temperature was varied between 120° C. and 260° C. in order to study the temperature effect for the growth of CdSe/CdS core/shell nanocrystals. For these reactions at different temperatures, the other reaction conditions and procedures were the same as the typical synthesis.

Example 5

Multigram-Scale Synthesis of CdSe/CdS Core/Shell Nanocrystals Using the Successive Ionic Layer Adsorption and Reaction (SILAR) Technique The SILAR procedure described above was readily extended to a large scale, multi-gram synthesis. In a typical large scale synthesis, 195 g of CdSe nanocrystal stock solution (3.5 nm in size, $5.87 \times 10^{-3}$ mmol of particles in hexanes) was mixed with 250 g of ODE and 75 g of ODA in a three-necked flask. After removal of hexanes and air under vacuum, the mixture was heated to 240° C. in an argon atmosphere, for the cation precursor and anion precursor injection and nanocrystal growth steps. With the same injection solutions used in the small scale synthesis, the amounts of the injection solutions injected for each step were as follows: 1) 27 mL of the Cd and S solution for the first Cd and S injection; 2) 37 mL of each injection solution for the second layer; 3) 48.6 mL of each injection solution for the third layer; 4) 61.8 mL of each injection solution for the fourth layer; and 5) 76.6 mL of each injection solution for the fifth layer. The reaction solution was rapidly stirred during injection, therefore is was not necessary to inject the Cd and S injection solutions in a dropwise manner. After this large scale reaction, the raw products were separated by acetone precipitation followed by centrifugation. The sample of argon-flow dried nanocrystals, after purification, weighed about 2.5 grams.

Example 6

Optical Measurements of the CdSe/CdS Core/Shell Nanocrystals

Absorption spectra were measured using an HP 8453 diode array spectrophotometer. Photoluminescence (PL) and photoluminescence excitation (PLE) spectra were examined using a HITACHI F-2500 fluorescence spectrophotometer. The photoluminescence (PL) quantum yield (QY) of samples was obtained using organic dyes with known quantum yields as the standard. Suitable methods and examples of this procedure are disclosed in: Peng, X.; Schlamp, M. C.; Kadavanich, A. V.; Alivisatos, A. P. *J. Am. Chem. Soc.* 1997, 119, 7019-7029; Manna, L.; Scher, E. C.; Li, L.-S.; Alivisatos, A. P. *J. Am. Chem. Soc.* 2002, 124, 7136-7145; Qu, L.; Peng, X. *J. Am. Chem. Soc.* 2002, 124, 2049-2055; each of which is incorporated herein by reference in its entirety.

Careful studies revealed that the PL QY of colloidal semiconductor nanocrystals determined by typical procedures varied somewhat when using different organic dyes as the PL QY standard. Accordingly, the PL QY data reported herein were obtained using R640 as the standard, which provided significantly lower values than those obtained when using other dyes, such as LD690. Both organic dyes (R640 and LD690) were purchased from Exciton.

Example 7

Transmission Electron Microscopy (TEM) Images of Nanocrystals

Low resolution TEM images of the nanocrystals described herein, for example, the CdSe/CdS core/shell nanocrystals, were obtained using a JOEL 100CX transmission electron microscope with 80 kV acceleration voltage. The CdSe/CdS core/shell nanocrystals samples examined were typically purified by either acetone precipitation from a chloroform solution, or hexanes/methanol extraction. Formvar® film-coated copper grids were dipped into hexanes or toluene solutions of the nanocrystals to deposit the nanocrystals onto the film. Randomly oriented nanocrystals on the TEM substrate were obtained by using a diluted nanocrystal solution, with an absorbance of the first absorption peak of the nanocrystals below approximately 0.05. If the absorbance of the first absorption peak was above about 0.2, densely packed monolayers and multilayers of nanocrystals were observed. Selected area electron diffraction patterns (SAED) were obtained with a camera length of 120 cm.

High resolution TEM pictures were obtained using a JEOL 2000 microscope, in which the nanocrystals were deposited onto thin carbon grids purchased from Ted Pella, Inc., Redding, Calif.

Example 8

X-Ray Powder Diffraction (XRD) Images of Nanocrystals

X-ray Powder Diffraction (XRD) patterns of the nanocrystals described herein, for example, the CdSe/CdS core/shell nanocrystals, were obtained using a Philips PW1830 X-ray diffractometer. In order to obtain meaningful diffraction patterns for the CdSe/CdS core/shell nanocrystals, the excess ODA ligands were thoroughly removed from a sample of the nanocrystals.

Example 9

Photo-Oxidation Experiments on Nanocrystals

The photo-oxidation tests on the nanocrystals described herein, for example, on the CdSe/CdS core/shell nanocrystals, were performed using either the standard method described in Aldana, J.; Wang, Y.; Peng, X. *J. Am. Chem. Soc.* 2001, 123, 8844 and Wang, Y. A.; Li, J. J.; Chen, H.; Peng, X. *J. Am. Chem. Soc.* 2002, 124, 2293-2298, or using a Coherent Inc. argon ion laser with 50-100 mW of a 514 nm beam, as described in Manna, L.; Scher, E. C.; Li, L.-S.; Alivisatos, A. P. *J. Am. Chem. Soc.* 2002, 124, 7136-7145, each of which is incorporated herein by reference in its entirety.

For the laser-related experiments, a light beam spot, 0.8 cm in diameter, was projected onto a sample by inserting a diverging lens in the beam path. Nanocrystal solutions, saturated with oxygen or argon, were compared under the same testing conditions. Photoluminescence spectra were measured before and after irradiation.

Example 10

Thin Film Deposition of CdSe Plain Core and CdSe/CdS Core/Shell Nanocrystals Plain core nanocrystals or core/shell nanocrystals were deposited onto glass or ITO (indium-doped tin oxide) substrates by spin coating the nanocrystals from toluene solutions. The PL spectra of the thin films were taken by placing the substrates at the cross-point of the excitation beam and the normal direction of the detector, with a 30° angle relative to both directions. The PL spectra of the two original solutions with the same absorbance at the excitation wavelength were compared. The PL spectra of the two thin films of CdSe nanocrystals and CdSe/CdS core/shell nanocrystals were compared by normalizing the PL intensity using the absorbance of thin films at the excitation wavelength.

Example 11

Surface Modification of CdSe Plain Core and CdSe/CdS Core/Shell Nanocrystals with Mercaptopropionic Acid Surface modification of both the CdSe plain core and CdSe/CdS core/shell nanocrystals with mercaptopropionic acid was performed using the standard procedure described in Aldana, J.; Wang, Y.; Peng, X. *J. Am. Chem. Soc.* 2001, 123, 8844. The UV-Vis and PL measurements were carried out using the purified nanocrystals dissolved in water.

Example 12

Synthesis of CdSe/ZnS Core/Shell Nanocrystals Using the Successive Ionic Layer Adsorption and Reaction (SILAR) Technique In a typical successive ionic layer adsorption and reaction (SILAR) technique preparation of CdSe/ZnS core/shell nanocrystals, alternating injections of the Zn and S injection solutions into a CdSe nanocrystal-containing solution were carried out. A stock solution of 2.44 g of CdSe nanocrystals in hexanes, 3.5 nm in diameter and $1.01 \times 10^{-4}$ mmol in hexanes, was mixed with 1.5 g of ODA and 5.0 g of ODE in a 25 mL, three-necked flask. The flask was then sealed and placed under vacuum at room temperature for 30 min to remove the hexanes, then heated to 100° C. while still under vacuum for another 5-10 min to remove any residual air from the system. After this procedure, the CdSe nanocrystal-containing solution was placed under an argon flow and the reaction mixture was further heated to 270° C. in preparation for injections. The first injection was made using 0.49 mL of the Zn injection solution (0.04 M). The amounts of the injection solutions were calculated for each subsequent injection using the method described above. To monitor the reaction, aliquots were taken at the first minute after injection and subsequently every 3-5 min, and absorption measurements of each aliquot were examined. If there was no observable change in the UV-Vis absorption spectrum for two successive aliquots 3-5 min separated, the injection of another shell component for either the same layer (nS) or the next layer ((n+1)Zn) was executed.

After no further UV-Vis peak shift was observed in 5 min following the fifth sulfur injection, the reaction was terminated by allowing the reaction mixture to cool to room temperature. The final product was purified by diluting the reaction solution with hexanes, and the contaminants were extracted from the hexane solution with methanol. Alternatively, the resulting nanocrystals were precipitated by adding acetone to the hexanes solution. Excess amines were further removed by dissolving the nanocrystals in chloroform and precipitating them with acetone.

Example 13

Synthesis of InAs/CdS Core/Shell Nanocrystals Using the Successive Ionic Layer Adsorption and Reaction (SEAR) Technique Plain InAs core nanocrystals (or simply, "cores") were synthesized using a method analogous to that described in Battaglia, D; Peng, X. *NanoLetters* 2002, 2(9), 1027, which is incorporated herein by reference in its entirety. Once the core InAs nanocrystals had grown to completion, cadmium injection solutions (CdO-oleic acid in ODE) and sulfur injection solutions (sulfur in ODE), prepared as detailed in the Examples herein, were added dropwise to the solution containing the InAs cores at about 250° C., according to a similar method as that used for the CdSe/CdS core/shell nanocrystals described herein. This synthesis method initially formed an alloyed layer of InCdS for the first few layers, but then became pure CdS for the layers subsequent to that.

Example 14

Synthesis of InAs/InP Core/Shell Nanocrystals Using the Successive Ionic Layer Adsorption and Reaction (SEAR) Technique Plain InAs core nanocrystals (cores) were synthesized using a method analogous to that described in Battaglia, D; Peng, X. *NanoLetters* 2002, 2(9), 1027, which is incorporated herein by reference in its entirety. Once the core InAs nanocrystals finished growing, the reaction solution was then cooled to 250° C. from 300° C. and tris(trimethylsilyl)phosphine in 1 gram octadecene (ODE) (0.05 mmol) was added to the reaction solution. The tris(trimethylsilyl)phosphine precursor reacted with the excess indium already in the solution, due to the 8:1 indium to arsenic molar ratio used for the InAs core nanocrystal formation, to form the InP layers. More tris(trimethylsilyl)phosphine precursor could be added in the same manner to increase the InP shell thickness. This one-pot, core/shell method enabled InP to be grown on the surface of the InAs nanocrystals without exposing them to the air, thus stabilizing the InAs nanocrystals from oxidation.

Example 15

Synthesis of CdS/CdSe Quantum Shell Nanocrystals Using the Successive Ionic Layer Adsorption and Reaction (SILAR) Technique A sample of CdS core nanocrystals of a known size and concentration was used to prepare a CdS reaction solution containing ODE as the solvent and octadecylamine (ODA) as the ligand. A typical reaction contained $5.0 \times 10^{-8}$ mol of CdS, however, the concentration did not need to be fixed as long as the precursor injections were enough to create a single monolayer on the surface of the cores. Once the CdS, 5 grams of ODE, and 1 gram of ODA were added to the reaction flask the reaction was heated up to 100° C. while under vacuum. When the reaction stopped bubbling, the solution was placed under an argon flow and heated up to 190° C. for CdSe shell growth. The Cd-Oleic acid and pure Se precursors in ODE (0.04 M each) were added in alternating injections at 190° C. The volume of each injection was selected to create one monolayer of CdSe on the surface of the CdS cores. Additional layers could be added by increasing the injection amounts to take into considerating the increase in size from the shell already grown. (core+0.7 nm).

Example 16

Synthesis of CdS/InP Quantum Shell Nanocrystals Using the Successive Ionic Layer Adsorption and Reaction (SILAR) Technique A sample of CdS core nanocrystals of a known size and concentration was used to prepare a CdS reaction solution containing ODE as the solvent and octadecylamine (ODA) as the ligand. A typical reaction contained $5.0 \times 10^{-8}$ mol of CdS, however, the concentration did not need to be fixed as long as the precursor injections were enough to create a single monolayer on the surface of the cores. Once the CdS, 5 grams of ODE, and 1 gram ODA were added to the reaction flask, the reaction was heated up to 100° C. while under vacuum. When the reaction stopped bubbling, the solution was placed under an argon flow and heated up to 180° C. for InP shell growth. The indium-Oleic acid and tris(trimethylsilylphosphine) precursors in ODE (0.04 M each) were added in alternating injections at 180° C. The volume of each injection was selected to create one monolayer of InP on the surface of the CdS cores.

Example 17

Synthesis of CdS/CdSe/CdS Quantum Well Nanocrystals Using the Successive Ionic Layer Adsorption and Reaction (SILAR) Technique A sample of CdS core nanocrystals of a known size and concentration was used to prepare a CdS reaction solution containing ODE as the solvent and oleic acid (OA) as the ligand. Oleic acid was used because it is a good ligand with respect to sustaining good PL emission properties for CdS, but not for CdSe. A typical reaction contained $5.0 \times 10^{-8}$ mol of CdS, however, the concentration did not need to be fixed as long as the precursor injections were enough to create a single monolayer on the surface of the cores. Once the CdS, 5 grams of ODE, and 1 gram of oleic acid were added to the reaction flask, the reaction was heated up to 100° C. while under vacuum. When the reaction stopped bubbling, the solution was put under an argon flow and heated up to 200° C. for the CdSe shell growth and 240° C. for the CdS growth. The Cd-Oleic acid and pure Se precursors in ODE (0.04 M each) were added in alternating injections at 200° C. The volume of each injection was selected to create one monolayer of CdSe on the surface of the CdS cores. The reaction temperature was then increased to 240° C., and alternating injections of Cd-Oleic acid and pure S in ODE (0.04 M each) were added to create the monolayers of CdS on the CdS/CdSe core/shell nanocrystals, and hence form the CdS/CdSe/CdS core/shell/shell nanocrystals.

Example 18

Synthesis of Dual-Emitting CdSe/ZnS/CdSe 0D-1D Hybrid Nanocrystals Using the Successive Ionic Layer Adsorption and Reaction (SILAR) Technique A sample of CdSe core nanocrystals of a known size and concentration was used to prepare a CdSe reaction solution containing ODE as the solvent and octadecylamine (ODA) as the ligand. A typical reaction contained $1.25 \times 10^{-8}$ mol of CdSe, however, the concentration did not need to be fixed as long as the precursor injections were enough to create a single monolayer on the surface of the cores. Once the CdSe, 5 grams of ODE, and 1 gram of ODA were added to the reaction flask, the reaction was heated up to 100° C. while under vacuum. Once the reaction stopped bubbling, the solution was put under an argon flow and heated up to 200° C. for the ZnS layering. The Zn-Oleic acid and pure S precursors in ODE (0.04 M each) were added in alternating injections at 200° C. in order to grow a single monolayer at a time of ZnS on the surface of the CdSe. Using this method, many layers of ZnS can be layered on in a controlled fashion. In one aspect, it was found that 2 to 4 monolayers gave excellent results. The reaction temperature was then decreased to 190° C. and Cd-Oleic acid and pure Se precursors in ODE (0.04M) were added in alternating injections in order to grow the CdSe monolayers. The CdSe could be layered as many times as needed. No secondary emission was seen for the first monolayer. In one aspect, the shell was not be layered to the extent that its emission overlapped that of the core, which would otherwise eliminate the detection of the core emission.

Example 19

Synthesis of Doped Nanocrystals Using the Successive Ionic Layer Adsorption and Reaction (SILAR) Technique Pre-synthesized ZnSe nanocrystals (10 mg) were added into a three-neck flask with ODE (3 g) and octadecylamine (2 g). Under the same experimental conditions discussed in Example 5, the solution was heated to about 200-260° C. Either Cu stearate or Mn stearate were used as the precursor for the Cu and Mn dopants, respectively. The growth of the nanocrystals was achieved by adding the Zn stearate solution and Se solution as usual SILAR procedures as disclosed herein. The dopants were added into the Zn solution as needed and in a concentration required in a given monolayer.

The invention claimed is:
1. A composition comprising:
  (a) substantially monodisperse core/shell nanocrystals, the core/shell nanocrystals comprising a core and a first shell overcoating the core, wherein the core comprises a II/VI compound or a III/V compound,
    the first shell comprises 3 or more monolayers of a II/VI compound or a III/V compound,
    the first shell and the core have different chemical compositions, and
    the core/shell nanocrystals have a size distribution having a standard deviation no greater than about 10% of a mean diameter of the nanocrystals;
  (b) a solvent; and
  (c) unreacted reactants and side products.
2. The composition of claim 1, wherein the first shell comprises 4 or more monolayers of the II/VI compound or the III/V compound.
3. The composition of claim 1, wherein the first shell comprises from 3 monolayers to 15 monolayers of the II/VI compound or the III/V compound.
4. The composition of claim 1, wherein the core/shell nanocrystals are as-prepared.
5. The composition of claim 1, wherein the core/shell nanocrystals have a size distribution having a standard deviation no greater than about 5% of a mean diameter of the nanocrystals.
6. The composition of claim 1, wherein the bandgap of the core is less than the bandgap of the first shell.
7. The composition of claim 1, wherein the core/shell nanocrystals exhibit a type-I band offset or a type-II band offset.
8. The composition of claim 1, wherein the core is selected from the group consisting of CdSe, CdS, CdTe, ZnSe, ZnS, ZnTe, HgSe, HgS, HgTe, ZnO, CdO, GaAs, InAs, GaP and InP;
  the first shell is selected from the group consisting of CdSe, CdS, CdTe, ZnSe, ZnS, ZnTe, HgSe, HgS, HgTe, ZnO, CdO, GaAs, InAs, GaP and InP.
9. The composition of claim 1, wherein the core/shell nanocrystals comprise CdSe/CdS, CdSe/ZnSe, CdSe/ZnS, CdS/ZnS, CdTe/CdSe, CdTe/CdS, CdTe/ZnTe, CdTe/ZnSe, CdTe/ZnS, ZnSe/ZnS, ZnTe/CdS, ZnTe/ZnSe, InAs/InP, InAs/CdSe, InAs/CdS, InAs/ZnS, InP/CdS, InP/ZnS, InP/ZnSe, InAs/InP/CdS or a mixture thereof.
10. The composition of claim 1, wherein the core/shell nanocrystals exhibit a photoluminescence quantum yield (PL QY) ranging from about 20% to about 40%.
11. The composition of claim 1, wherein the core/shell nanocrystals have a luminescence at a wavelength from about 400 nm to about 1000 nm.
12. The composition of claim 1, wherein the core/shell nanocrystals exhibit a photoluminescence emission line characterized by a FWHM of about 50 nm or less.
13. The composition of claim 1, wherein the core/shell nanocrystals exhibit a photoluminescence emission line characterized by a FWHM of about 40 nm or less.
14. The composition of claim 1, wherein the core/shell nanocrystals exhibit a photoluminescence emission line characterized by a FWHM of about 28 nm or less when the core material comprises CdSe.
15. The composition of claim 1, wherein the first shell of the core/shell nanocrystals is a quantum shell.
16. The composition of claim 15, wherein photogenerated excitons are radially confined to the quantum shell.
17. The composition of claim 15, wherein the core of the core/shell nanocrystals comprises an insulator.
18. The composition of claim 15, wherein the core/shell nanocrystals comprise CdS/CdSe, CdS/InP, CdS/CdTe, ZnS/

CdS, ZnS/CdSe, ZnS/ZnSe, ZnS/CdTe, ZnSe/CdSe, ZnSe/InP, CdS/InAs, CdSe/InAs, ZnSe/InAs, ZnS/InAs, InP/InAs or a mixture thereof.

19. A composition comprising:
(a) core/shell/shell nanocrystals, the core/shell/shell nanocrystals comprising a first shell overcoating the core and a second shell overcoating the first shell, wherein the core comprises a II/VI compound or a III/V compound,
the first shell and the second shell each comprise a II/VI compound or a III/V compound, the first shell and the core have different chemical compositions, the first shell and the second shell have different chemical compositions, at least one of the first shell and the second shell comprises 3 or more monolayers of the II/VI compound or the III/V compound, and the core/shell/shell nanocrystals have a size distribution having a standard deviation no greater than about 10% of a mean diameter of the nanocrystals;
(b) a solvent; and
(c) unreacted reactants and side products.

20. The composition of claim 19, wherein the first shell comprises 3 or more monolayers of the II/VI compound or the III/VI compound.

21. The composition of claim 19, wherein the second shell comprises 3 or more monolayers of the II/VI compound or the III/VI compound.

22. The composition of claim 19, wherein the core/shell/shell nanocrystals are as-prepared.

23. The composition of claim 19, wherein the core/shell/shell nanocrystals are quantum wells.

24. The composition of claim 23, wherein the core and the second shell comprise the same II/VI compound or III/V compound.

25. The composition of claim 19, wherein the bandgap of the first shell is less than the bandgap of the core and less than the bandgap of the second shell.

26. The composition of claim 23, wherein the quantum wells comprise CdS/CdSe/CdS, CdS/CdSe/ZnSe, CdS/CdSe/ZnS, ZnSe/CdSe/CdS, ZnSe/CdSe/ZnSe, ZnSe/CdSe/ZnS, ZnS/CdSe/ZnS, ZnS/CdSe/CdS, ZnS/CdSe/ZnSe, ZnS/CdS/ZnS, ZnS/ZnSe/ZnS, CdS/InP/CdS, CdS/InP/ZnSe, CdS/InP/ZnS, ZnSe/InP/ZnSe, ZnSe/InP/CdS, ZnSe/InP/ZnS, ZnS/InP/ZnS, ZnS/InP/CdS, ZnS/InP/ZnSe, CdS/InAs/CdS, CdS/InAs/ZnSe, CdS/InAs/ZnS, ZnSe/InAs/ZnSe, ZnSe/InAs/CdS, ZnSe/InAs/ZnS, ZnS/InAs/ZnS, ZnS/InAs/CdS, ZnS/InAs/ZnSe, CdSe/InAs/CdSe, CdSe/InAs/CdS, CdSe/InAs/ZnS, CdSe/InAs/ZnSe, InAs/InP/CdS, or a mixture thereof.

27. The composition of claim 19, wherein the core comprises an insulator.

28. The composition of claim 19, wherein the core/shell/shell nanocrystals have a size distribution having a standard deviation no greater than about 5% of a mean diameter of the nanocrystals.

29. The composition of claim 23, wherein the quantum wells exhibit a photoluminescence quantum yield ranging from about 10% to about 50%.

30. The composition of claim 23, wherein the quantum wells exhibit a photoluminescence quantum yield ranging from about 20% to about 50%.

31. The composition of claim 15, wherein the nanocrystals exhibit a photoluminescence quantum yield ranging from about 10% to about 20%.

32. The composition of claim 15, wherein the nanocrystals exhibit a photoluminescence emission line characterized by a FWHM of about 60 nm or less.

33. The composition of claim 15, wherein the nanocrystals exhibit a photoluminescence emission line characterized by a FWHM of about 40 nm or less.

34. The composition of claim 15, wherein the nanocrystals exhibit a photoluminescence emission line characterized by a FWHM of about 30 nm or less.

35. The composition of claim 15, wherein the nanocrystals have a size distribution having a standard deviation no greater than about 10% of a mean diameter of the nanocrystals.

36. A composition comprising:
(a) substantially monodisperse core/shell nanocrystals, the core/shell nanocrystals comprising a core and a first shell overcoating the core, wherein the core comprises a II/VI compound or a III/V compound,
the first shell comprises 2 or more monolayers of a II/VI compound or a III/V compound,
the first shell and the core have different chemical compositions, and
the core/shell nanocrystals have a size distribution having a standard deviation no greater than about 10% of a mean diameter of the nanocrystals;
(b) a solvent; and
(c) unreacted reactants and side products.

37. The composition of claim 1, wherein the first shell comprises 5 or more monolayers of the II/VI compound or the III/V compound.

* * * * *